US008216495B2

(12) United States Patent
Janssens et al.

(10) Patent No.: US 8,216,495 B2
(45) Date of Patent: Jul. 10, 2012

(54) PREPARATION METHOD FOR SOLID DISPERSIONS

(75) Inventors: Sandrien Janssens, Wilsele (BE); Guy Van Den Mooter, Pellenberg (BE)

(73) Assignee: Formac Pharmaceuticals N.V., Leuven (BE)

( * ) Notice: Subject to any disclaimer, the term of this patent is extended or adjusted under 35 U.S.C. 154(b) by 114 days.

(21) Appl. No.: 12/934,232

(22) PCT Filed: Mar. 25, 2009

(86) PCT No.: PCT/EP2009/053542
§ 371 (c)(1),
(2), (4) Date: Sep. 23, 2010

(87) PCT Pub. No.: WO2009/118356
PCT Pub. Date: Oct. 1, 2009

(65) Prior Publication Data
US 2011/0018154 A1 Jan. 27, 2011

Related U.S. Application Data

(60) Provisional application No. 61/070,840, filed on Mar. 25, 2008, provisional application No. 61/106,536, filed on Oct. 17, 2008.

(51) Int. Cl.
*B29B 9/00* (2006.01)
(52) U.S. Cl. .......................................................... 264/5
(58) Field of Classification Search .................. None
See application file for complete search history.

(56) References Cited

U.S. PATENT DOCUMENTS

| 5,985,248 A | 11/1999 | Gordon et al. |
|---|---|---|
| 6,077,543 A | 6/2000 | Gordon et al. |
| 6,365,190 B1 | 4/2002 | Gordon et al. |
| 2005/0003000 A1* | 1/2005 | Einig et al. ............. 424/451 |
| 2005/0107498 A1* | 5/2005 | Kolter et al. ............. 524/35 |

FOREIGN PATENT DOCUMENTS

| WO | WO 2007/115381 A2 | 10/2007 |
| WO | WO 2008/080773 A1 | 7/2008 |

OTHER PUBLICATIONS

International Search Report of International Application No. PCT/EP2009/053542 dated Dec. 15, 2009 (date of completion of search) and Dec. 22, 2009 (date of mailing of report).

Written Opinion of the International Search Authority for International Application No. PCT/EP2009/053542 dated Dec. 22, 2009 (date of mailing).
Official Communication from the European Patent Office for European Patent Application No. 09 725 902.2, dated Dec. 2, 2010.
"Guidance for Industry: Waiver of in Vivo Bioavailability and Bioequivalence Studies for Immediate-Release Solid Oral Dosage Forms Based on a Biopharmaceutics Classification System," U.S. Department of Health and Human Services Food and Drug Administration Center for Drug Evaluation and Research (CDER), Aug. 2000.
Lindenberg et al., "Classification of Orally Administered Drugs on the World Health Organization Model List of Essential Medicines According to the Biopharmaceutics Classification System," *European Journal of Pharmaceutics and Biopharmaceutics* 58:265-278, 2004.
"WHO Technical Report Series: WHO Expert Committee on Specifications for Pharmaceutical Preparations," Fortieth Report, World Health Organization, Geneva, 937:401-437, 2006.
Summons to attend oral proceedings pursuant to Rule 115(1) EPC for European Patent Application No. 09725902.2, dated Mar. 28, 2011.

\* cited by examiner

*Primary Examiner* — Mary F Theisen
(74) *Attorney, Agent, or Firm* — Clark & Elbing LLP

(57) ABSTRACT

A method of preparation of a solid dispersion of a polyvinyl alcohol-polyethylene glycol graft copolymer (PVA-PEG graft co-polymer), such as Kollicoat IR with a BCS Class II drug or a BCS Class IV drug, whereby the method comprises: a) dissolving the polyvinyl alcohol-polyethylene glycol graft copolymer (PVA-PEG graft co-polymer) separately in a water/first alcohol mixture; and b) dissolving the BCS Class II drug or a BCS Class IV drug, in a mixture of a second alcohol with a non alcoholic organic solvent in which the compound has an high solubility; and c) mixing the both solutions to obtain a third solution with a total amount of solved solid of 1 to 15 g per 100 ml, and optionally having an acid, including inorganic acids including hydrohalic acids, e.g. hydrochloric or hydrobromic acid; sulfuric; nitric; phosphoric and the like acids; or organic acids including acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids in the mixture of both the solutions to achieve an acid pH; and d) spray drying the third solution.

20 Claims, 6 Drawing Sheets

US 8,216,495 B2

PREPARATION METHOD FOR SOLID DISPERSIONS

CROSS REFERENCE TO RELATED APPLICATIONS

This application is the U.S. National Stage of International Application No. PCT/EP2009/053542, filed Mar. 25, 2009, which claims the benefit of U.S. Patent Application No. 61/070,840, filed Mar. 25, 2008 and U.S. Patent Application No. 61/106,536, filed Oct. 17, 2008.

FIELD OF THE INVENTION

The invention concerns a method for preparation of one or more poorly soluble drugs in a solid dispersion by spray drying and in particular the use of Kollicoat IR and a specific compound such as Itraconazole solid dispersions.

BACKGROUND OF THE INVENTION

The development of new pharmaceutical compounds is often impaired by their problematic aqueous solubility, which leads to incomplete dissolution into the gastro-intestinal juices and hence, insufficient bioavailability. Therefore, the improvement of dissolution and solubility of poorly soluble drugs is a major field of interest for formulation scientists. The formulation of solid dispersions, which are prepared by dispersing the poorly soluble active compound into an inert hydrophilic carrier at the solid state, is a possible means of increasing bioavailability.

WO 03/063822A discloses a process for producing a pharmaceutical composition comprising the steps: (a) forming a feed solution comprising a drug, a concentration-enhancing polymer and a solvent; (b) directing said feed solution to a spray-drying apparatus comprising (i) a drying chamber having a volume $V_{dryer}$ and a height H, (ii) atomizing means for atomizing said feed solution into droplets, (iii) a source of heated drying gas for drying said droplets, said source delivering said drying gas to said drying chamber at a flow rate of G, and (iv) gas-dispersing means for dispersing said drying gas into said drying chamber, said gas-dispersing means causing organized plug flow of said drying gas, wherein $V_{dryer}$ is measured in m³, H is at least 1 m, G is measured in m³/sec, and wherein the following mathematical relationship is satisfied $[V_{dryer}/G] \geq 10$ seconds; (c) atomizing said feed solution into droplets in said drying chamber by said atomizing means, said droplets having an average diameter of at least 50 µm and a $D_{10}$ of at least 10 µm; (d) contacting said droplets with said heated drying gas to form particulates of a solid amorphous dispersion of said drug and said concentration-enhancing polymer; and (e) collecting said particulates, wherein said concentration-enhancing polymer is present in said solution in an amount sufficient that said solid amorphous dispersion provides concentration enhancement of said drug in a use environment relative to a control composition consisting essentially of an equivalent amount of said drug alone.

WO 2005/011636A discloses a process for forming a pharmaceutical composition comprising a solid amorphous dispersion comprising a drug and a polymer, comprising the steps of: (a) providing a drying apparatus having an atomizer connected to a drying chamber, said drying chamber having an inlet and an outlet; (b) forming a spray solution by dissolving said low-solubility drug and said polymer in a solvent, wherein said polymer is selected from the group consisting of hydroxypropyl methyl cellulose acetate succinate, hydroxypropyl methyl cellulose, hydroxypropyl methyl cellulose phthalate, carboxymethyl ethyl cellulose, cellulose acetate phthalate, and cellulose acetate trimellitate; (c) spraying said spray solution through said atomizer into said chamber to form droplets having a volume average size of less than 500 µm; (d) flowing a drying gas through said inlet at a flow rate and a temperature $T_{in}$ such that said droplets solidify in less than about 20 seconds to form said solid amorphous dispersion of said low-solubility drug in said polymer; (e) wherein said solid amorphous dispersion of said low-solubility drug in said polymer provides either concentration enhancement or faster dissolution of said low-solubility drug in an aqueous use environment relative to a control composition consisting of said low-solubility drug alone; wherein a feed rate of said spray solution is at least 10 kg/hr, and said feed rate of said spray solution and said $T_{in}$ of said drying gas are controlled so that said drying gas at said outlet has a temperature $T_{out}$, and said $T_{out}$ is less than said boiling point of said solvent.

US 2008/0248117A corresponding to PCT/EP2006/062788 published as WO 2006/0131481A on Dec. 14, 2006 discloses a process for producing solutions in powder or granule form of slightly soluble substances, wherein said slightly soluble substance is in the form of a molecular dispersion in an excipient matrix, comprising atomizing a solution of the active ingredient and matrix excipients by heating an aqueous suspension of said slightly soluble substance in the presence of the matrix excipients to temperatures above the boiling point under atmospheric pressure, dissolving the slightly soluble substance, and converting said solution of slightly soluble substance and matrix excipients by atomizing and drying into a solid form, wherein the temperature of the spray solution before feeding into the atomizing apparatus is in the range of from 90° C. to 350° C.

WO 2007/115381A with the same inventors as the present application discloses a medical dosage form of enhanced solubility and dissolution rate in an aqueous environment of low aqueous solubility drugs, characterised in that it comprises a solid dispersion of at least one drug of low aqueous solubility in graft copolymer of 1) water-soluble chains of the vinyl polymer on 2) a polymer chain of water-soluble waxy of alcohols with general formula $C_{2n}H_{4n+2}O_{n+1}$ or a polymer chain of polyethylene glycols, polyalkylene glycols, polypropylene glycols, polyisobutylene glycols or polymethyl-pentene glycols. WO 2007/115381A further discloses that the form of solid dispersions of drug in the graft copolymer may be obtainable by hot-stage extrusion or spray-drying.

WO 2008/016260A published Feb. 2, 2008 discloses a method of preparing a solid dispersion comprising the steps of: dissolving fenofibrate in an organic solvent, and mixing with 20-200 parts by weight of a water-soluble polymer and 5-50 parts by weight of a surfactant on the basis of 100 parts by weight of fenofibrate to produce a mixed solution, and spray-drying the mixed solution to obtain a solid dispersion comprising an amorphous fenofibrate.

WO 2008/077591A published Jul. 3, 2008 discloses a process for making a solid dispersion, said solid dispersion comprising (4R)-4-[N'-methyl-N'-(3,5-bistrifluoro-methyl-benzoyl)-amino]-4-(3,4-dichlorobenzyl)-but-2-enoic acid N-[(R)-ε-caprolactam-3-yl]-amide or a pharmaceutically acceptable salt or solvate thereof, and a carrier, said process comprising the steps of (a) dissolving or suspending (4R)-4-[N'-methyl-N'-(3,5-bistrifluoromethyl-benzoyl)-amino]-4-(3,4-dichlorobenzyl)-but-2-enoic acid N-[(R)-ε-caprolactam-3-yl]-amide or a pharmaceutically acceptable salt or solvate thereof and the carrier in a solvent to form a solution or suspension; and (b1) spray drying the solution or suspension to give a solid dispersion in dry powder form or (b2) or spray granulating the solution or suspension on at least one inert filler excipient and at least one anti-sticking agent.

U.S. Pat. No. 6,077,543 discloses a method for preparing a dry powder composition, said method comprising: preparing an aqueous solution of a hydrophilic component; preparing an organic solution of a hydrophobic component in an organic solvent; and delivering the aqueous solution containing the hydrophilic component to an atomizer; delivering the organic solution containing the hydrophobic solution to the atomizer separately from the aqueous solution containing the hydrophilic solution; atomizing the two solutions together in the atomizer to produce droplets containing both solutions; spray drying the droplets of the aqueous solution and the organic solution to form dry particles comprising a mixture of the hydrophilic and hydrophobic component, the hydrophobic component preferably comprising a hydrophobic drug.

U.S. Pat. No. 5,985,248 discloses a method for preparing a dry powder composition, said method comprising: at least partially dissolving a hydrophilic component consisting of a hydrophilic excipient or mixture of excipients in an organic solvent or cosolvent system; at least partially dissolving a hydrophobic component consisting of a hydrophobic drug in the same organic solvent or cosolvent system to produce an organic solution, wherein the organic solvent or cosolvent system is selected so that the hydrophilic component has a concentration in the range from 1 mg/ml to 100 mg/ml and the hydrophobic component has a concentration in the range from 0.01 mg/ml to 10 mg/ml; and spray drying the organic solution, to form particles comprising a mixture of the hydrophilic and hydrophobic components, the hydrophobic component preferably comprising a hydrophobic drug.

SUMMARY OF THE INVENTION

In order to prepare a solid dispersion via the solvent technique, all ingredients, drug and carrier, have to dissolve in a common solvent. Consequently, the solvent is evaporated and the resulting solid dispersion precipitates. The weak base, Itraconazole, has an extremely low aqueous solubility, 1 ng/ml at pH=7; 4 µg/ml at pH=1. The hydrophilic polymer, Kollicoat IR, is soluble in water and in 50/50 V/V water/ethanol mixtures. However, by dissolving Kollicoat IR, separately in a 50/50 V/V water/ethanol mixture and Itraconazole in a 50/50 V/V dichloromethane/ethanol mixture, a fairly clear solution can be obtained when the Itraconazole solution is added to the Kollicoat IR solution. If hydrochloric acid is added to the Kollicoat IR solution, the resulting Itraconazole/Kollicoat IR solution is completely clear.

Aspects of the present invention are realized by a method of preparation of a solid dispersion of a water soluble polymer, preferably a polyvinyl alcohol-polyethylene glycol graft polymer, and a BCS class II drug or a BCS class IV drug, comprising the steps of:
a) dissolving a water-soluble polymer in water or a mixture comprising water and at least one first alcohol to form a first solution; and
b) dissolving at least one BCS class II drug or at least one BCS class IV drug in a mixture comprising at least one second alcohol and at least one non-alcoholic organic solvent to form a second solution; and
c) mixing the first and the second solution to obtain a mixture of the first and second solutions; and
d) transferring the mixture of the first and second solutions to a device for spray drying; and
e) spray drying the mixture of the first and second solutions. The mixture of the first and second solutions is preferably at least a metastable solution.

Aspects of the present invention are also realized by a method of preparation of a solid dispersion of a polyvinyl alcohol-polyethylene glycol graft copolymer (PVA-PEG graft co-polymer), such as Kollicoat IR with a BCS Class II drug or a BCS Class IV drug, whereby the method comprises:
a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and
b) dissolving the BCS Class II drug or a BCS Class IV drug, in a mixture of a alcohol with a non alcoholic organic solvent in which the triazole compound has an high solubility with, preferably a mixture of a straight-chain alcohol with the organic solvent or most preferably a mixture of ethanol with the organic solvent; and
c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids and preferably hydrochloric acid, in the mixture of both the solutions to achieve an acid pH for instance a pH lower than 3 e.g. by adding the acid to the mixture or optionally having a base, preferably a suitable base such as, for example, sodiumhydroxide, sodiumhydride, triethylamine or N,N-di-isopropyl-ethylamine or the like, in the mixture of both the solutions to achieve a basic pH for instance above 10 e.g. by adding the base to the mixture; and
d) spray drying such solution.

Further embodiments of the present invention are disclosed in the detailed description.

DETAILED DESCRIPTION

Definitions

Figure 1:
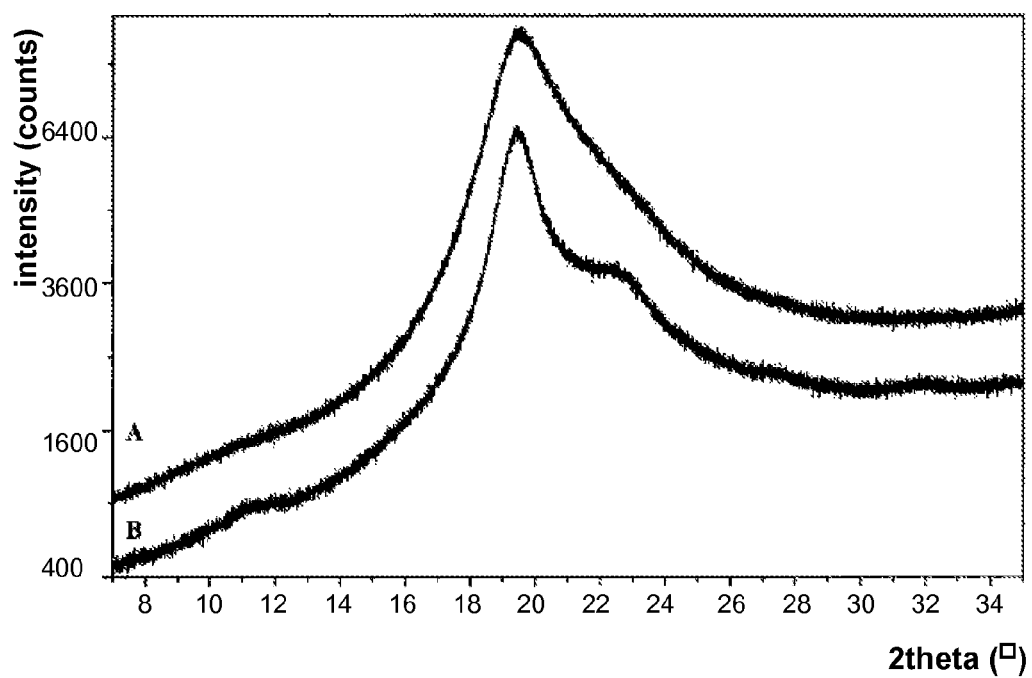
FIG. 1: X-ray diffractograms of A: Kollicoat IR spray dried from single inlet spray nozzle, and B: unprocessed Kollicoat IR.

The term "practically insoluble" as used herein applies to drugs that are essentially totally water-insoluble or are at least poorly water-soluble. More specifically, the term is applied to any drug that has a dose (mg) to aqueous solubility (mg/ml) ratio greater than 100 ml, where the drug solubility is that of the neutral (for example, free base or free acid) form in unbuffered water. This meaning is to include, but is not to be limited to, drugs that have essentially no aqueous solubility (less than 1.0 mg/ml).

Based on the BCS, "poorly water-soluble" can be defined as compounds whose highest dose is not soluble in 250 mL or less of aqueous media from pH 1.2 to 7.5 at 37° C. See Cynthia K. Brown, et al., "Acceptable Analytical Practices for Dissolution Testing of Poorly Soluble Compounds", Pharmaceutical Technology (December 2004).

According to the manual, Pharmaceutics (M. E. Aulton) for any solvent solubility is defined as the amount of a solvent (g) required to solve 1 g op the compounds whereby the following solubility qualification are defined: 10-30 g (soluble); 30-100 g ("sparingly soluble"); 100-1000 g ("slightly soluble"); 1000-10000 g ("very slightly soluble" or "poorly soluble") and more than 10000 g (practically insoluble).

The term "drug" will be widely understood and denotes a compound having beneficial prophylactic and/or therapeutic properties when administered to, for example, humans. Further, the term "drug per se" is used throughout this specification for the purposes of comparison, and means the drug when in an aqueous solution/suspension without the addition of any excipients.

The term "bioactive species" is an abbreviation of the term "biologically active species" and in the present application has the same meaning as "drug" and these terms are used interchangeably in the present application.

The term "bioactive compound" is an abbreviation of the term "biologically active compound". One skilled in the art would regard a drug as a bioactive compound.

The term a "solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion will be called "a solid solution" hereinafter. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to particles having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions within the particles distinctively marked by some physical feature, small in size compared to the size of the particle as a whole, and evenly and randomly distributed throughout the particle.

A "metastable solution" is a solution in a non-equilibrium state that persists for some period of time. Although potentially unstable and transient it can survive for a relatively long-lived state.

Method of Preparation of a Solid Dispersion of a Water-soluble Polymer with a Bioactive Compound The present invention also concerns a method of preparation of a solid dispersion of a polyvinyl alcohol-polyethylene glycol graft copolymer (PVA-PEG graft co-polymer), such as Kollicoat IR, with a bioactive compound wherein the polar surface area (PSA) is in the range from 60 Å$^2$ to 200 Å$^2$, 2) a bioactive compound with a partition coefficient (X log P) in the range from 4 to 9, 3) a bioactive compound with more than 10 freely rotating bonds, 4) a bioactive compound with polar surface area (PSA) in the range from 80 and 200, a partition coefficient in the range from 3 and 8 and with 8 to 16 freely rotating bonds or 5) a bioactive compound with a Polar Surface Area lager than 80 Å, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the bioactive compound in mixture of a alcohol with a non alcoholic organic solvent in which the triazole compound has a high solubility with, preferably a mixture of a straight-chain alcohol with the organic solvent or most preferably a mixture of ethanol with the organic solvent; and c) mixing the both solutions to obtain a total amount of dissolved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention also concerns a method of preparation of a solid dispersion of a polyvinyl alcohol-polyethylene glycol graft copolymer (PVA-PEG graft co-polymer), such as Kollicoat IR with an hydrophobic drug, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the hydrophobic drug in a mixture of a alcohol with a non alcoholic organic solvent in which the triazole compound has an high solubility with, preferably a mixture of a straight-chain alcohol with the organic solvent or most preferably a mixture of ethanol with the organic solvent; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a bioactive compound wherein the polar surface area (PSA) is in the range from 60 $\text{Å}^2$ to 200 $\text{Å}^2$, 2) a bioactive compound with a partition coefficient (X log P) in the range from 4 to 9, 3) a bioactive compound with more than 10 freely rotating bonds, 4) a bioactive compound with polar surface area (PSA) in the range from 80 and 200, a partition coefficient in the range from 3 and 8 and with 8 to 16 freely rotating bonds or 5) a bioactive compound with a Polar Surface Area lager than 80 Å, whereby the method comprises:

a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the bioactive compound in mixture of a non alcoholic organic solvent/a straight-chain alcohol in the ratio of 30-50/30-50 V/V or most preferably of 50/50 V/V or about 50/50V, preferably a mixture of non alcoholic organic solvent/ethanol mixture in the ratio of 30-50/30-50 V/V or most preferably of 50/50 V/V or about 50/50V; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a BCS Class II drug, whereby the method comprises:

a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the BCS Class II drug or a BCS Class IV drug in mixture of a non alcoholic organic solvent/a straight-chain alcohol in the ratio of 30-50/30-50 V/V or most preferably of 50/50 V/V or about 50/50V, preferably a mixture of non alcoholic organic solvent/ethanol mixture in the ratio of 30-50/30-50 V/V or most preferably of 50/50 V/V or about 50/50V; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a hydrophobic drug, whereby the method comprises:

a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the hydrophobic drug in mixture of a non alcoholic organic solvent/a straight-chain alcohol in the ratio of 30-50/30-50 V/V or most preferably of 50/50 V/V or about 50/50V, preferably a mixture of non alcoholic organic solvent/ethanol mixture in the ratio of 30-50/30-50 V/V or most preferably of 50/50 V/V or about 50/50V; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention also concerns a method of preparation of a solid dispersion of a triazole compound such as 1) Itraconazole, 2) an Itraconazole derivative, 3) a triazole compound wherein the polar surface area (PSA) is in the range from 60 Å2 to 200 Å2, preferably from 70 Å2 to 160 Å2, more preferably form 80 Å2 to 140 Å2, yet more preferably from 90 Å2 to 120 Å2, and most preferably from 95 Å2 to 110 Å2, 4) a triazole compound with a partition coefficient (X log P) in the range from 4 to 9, more preferably in the range from 5 to 8 and most preferably in the range from 6 to 7, 5) a triazole compound with more than 10 freely rotating bonds, 6) triazole compound with polar surface area (PSA) in the range from 80 and 200, a partition coefficient in the range from 3 and 8 and with 8 to 16 freely rotating bonds or 7) a triazole compound with a Polar Surface Area lager than 80 521 . with a polyvinyl alcohol-polyethylene glycol graft copolymer (PVA-PEG graft co-polymer), such as Kollicoat IR, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the triazole compound in mixture of dichloromethane/alcohol preferably a mixture of dichloromethane/straight-chain alcohol preferably a mixture of ethanol with dichloromethane; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a bioactive compound wherein the polar surface area (PSA) is in the range from 60 Å2 to 200 Å2, preferably from 70 Å2 to 160 Å2, more preferably form 80 Å2 to 140 Å2, yet more preferably from 90 Å2 to 120 Å2. and most preferably from 95 Å2 to 110 Å2, 2) a bioactive compound with a partition coefficient (X log P) in the range from 4 to 9, more preferably in the range from 5 to 8 and most preferably in the range from 6 to 7, 3) a bioactive compound with more than 10 freely rotating bonds, 4) a bioactive compound with polar surface area (PSA) in the range from 80 and 200, a partition coefficient in the range from 3 and 8 and with 8 to 16 freely rotating bonds or 5) a bioactive compound with a Polar Surface Area lager than 80 Å, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the bioactive compound in mixture of dichloromethane/alcohol preferably a mixture of dichloromethane/straight-chain alcohol preferably a mixture of ethanol with dichloromethane; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a BCS Class II drug or a BCS Class IV drug, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the BCS Class II drug or a BCS Class IV drug in mixture of dichloromethane/alcohol preferably a mixture of dichloromethane/straight-chain alcohol preferably a mixture of ethanol with dichloromethane; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having an base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with an hydrophobic drug, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the hydrophobic drug in mixture of dichloromethane/alcohol preferably a mixture of dichloromethane/straight-chain alcohol preferably a mixture of ethanol with dichloromethane; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a bioactive compound wherein the polar surface area (PSA) is in the range from 60 $Å^2$ to 200 $Å^2$, 2) a bioactive compound with a partition coefficient (X log P) in the range from 4 to 9, 3) a bioactive compound with more than 10 freely rotating bonds, 4) a bioactive compound with polar surface area (PSA) in the range from 80 and 200, a partition coefficient in the range from 3 and 8 and with 8 to 16 freely rotating bonds or 5) a bioactive compound with a Polar Surface Area lager than 80 Å, whereby the method comprises:

a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the bioactive compound in a mixture of dichloromethane/alcohol preferably a mixture of dichloromethane/straight-chain alcohol and more preferably a mixture of dichloromethane/ethanol whereby the ratio of the fluids is in the range of 30-50/30-50 V/V or most preferably of 50/50 V/V or about 50/50V; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a BCS Class II drug or a BCS Class IV drug, whereby the method comprises:

a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the BCS Class II drug or a BCS Class IV drug in a mixture of dichloromethane/alcohol preferably a mixture of dichloromethane/straight-chain alcohol and more preferably a mixture of dichloromethane/ethanol whereby the ratio of the fluids is in the range of 30-50/30-50 V/V or most preferably of 50/50 V/V or about 50/50V; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with an hydrophobic drug, whereby the method comprises a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the hydrophobic drug in a mixture of dichloromethane/alcohol preferably a mixture of dichloromethane/straight-chain alcohol and more preferably a mixture of dichloromethane/ethanol whereby the ratio of the fluids is in the range of 30-50/30-50 V/V or most preferably of 50/50 V/V or about 50/50V; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

The present invention concerns also a method of preparation of a solid dispersion of a polyvinyl alcohol-polyethylene glycol graft copolymer (PVA-PEG graft co-polymer), such as Kollicoat IR with a practically insoluble drug a poorly water-soluble drug or a drug that is very slightly soluble or practically insoluble in water, whereby the method comprises:

a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the a practically insoluble drug, a poorly water-soluble drug or a drug that is very slightly soluble or practically insoluble in water, in a mixture of a alcohol with a non alcoholic organic solvent in which the triazole compound has an high solubility with, preferably a mixture of a straight-chain alcohol with the organic solvent or most preferably a mixture of ethanol with the organic solvent; and c) mixing the both solutions to obtain a total amount of solved solid of 1 to 15 g per 100 ml and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

In another embodiment, the present invention is concerned with a method of preparation of a solid dispersion of a water soluble polymer and a BCS class II drug or a BCS class IV drug, comprising the steps of:

a) dissolving a water-soluble polymer in water or a mixture comprising water and at least one first alcohol to form a first solution; and b) dissolving at least one BCS class II drug or at least one BCS class IV drug in a mixture comprising at least one second alcohol and at least one non-alcoholic organic solvent to form a second solution; and c) mixing the first and the second solution to obtain a third solution; and d) transferring the third solution to a device for spray drying; and e) spray drying the third solution.

An embodiment of the present invention concerns a method of preparation of a solid dispersion of a triazole compound such as 1) Itraconazole, 2) an Itraconazole derivative, 3) a triazole compound wherein the polar surface area (PSA) is in the range from 60 Å$^2$ to 200 Å$^2$, preferably from 70 Å$^2$ to 160 Å$^2$, more preferably form 80 Å$^2$ to 140 Å$^2$, yet more preferably from 90 Å$^2$ to 120 Å$^2$, and most preferably from 95 Å$^2$ to 110 Å$^2$, 4) a triazole compound with a partition coefficient (X log P) in the range from 4 to 9, more preferably in the range from 5 to 8 and most preferably in the range from 6 to 7, 5) a triazole compound with more than 10 freely rotating bonds, 6) triazole compound with polar surface area (PSA) in the range from 80 and 200, a partition coefficient in the range from 3 and 8 and with 8 to 16 freely rotating bonds or 7) a triazole compound with a Polar Surface Area lager than 80 Å. with a polyvinyl alcohol-polyethylene glycol graft copolymer (PVA-PEG graft co-polymer), such as Kollicoat IR, whereby the method comprises:

a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ratio of 30-50/30-50 V/V or most preferably of 50/50 V/V or about 50/50V; and b) dissolving the triazole compound in mixture of a alcohol with a non alcoholic organic solvent in which the triazole compound has an high solubility with, preferably a mixture of a straight-chain alcohol with the organic solvent or most preferably a mixture of ethanol with the organic solvent whereby the ratio of the fluids is in the range of 30-50/30-50 V/V or most preferably of 50/50 V/V or about 50/50V; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

In another embodiment of the present invention concerns a method of preparation of a solid dispersion of a triazole compound such as 1) Itraconazole, 2) an Itraconazole derivative, 3) a triazole compound wherein the polar surface area (PSA) is in the range from 60 $Å^2$ to 200 $Å^2$, preferably from 70 $Å^2$ to 160 $Å^2$, more preferably form 80 $Å^2$ to 140 $Å^2$, yet more preferably from 90 $Å^2$ to 120 $Å^2$. and most preferably from 95 $Å^2$ to 110 $Å^2$, 4) a triazole compound with a partition coefficient (X log P) in the range from 4 to 9, more preferably in the range from 5 to 8 and most preferably in the range from 6 to 7, 5) a triazole compound with more than 10 freely rotating bonds, 6) triazole compound with polar surface area (PSA) in the range from 80 and 200, a partition coefficient in the range from 3 and 8 and with 8 to 16 freely rotating bonds or 7) a triazole compound with a Polar Surface Area lager than 80 Å. with a polyvinyl alcohol-polyethylene glycol graft copolymer (PVA-PEG graft co-polymer), such as Kollicoat IR, whereby the method comprises a) dissolving the polyvinyl alcohol-polyethylene glycol graft copolymer (PVA-PEG graft co-polymer), such as Kollicoat IR, separately in a water/straight-chain alcohol mixture with the ration of 30-50/30-50 V/V or most preferably of 50/50 V/V or about 50/50V preferably such mixture of water/ethanol mixture with the ration of 30-50/30-50 V/V or most preferably of 50/50 V/V or about 50/50V; and b) dissolving the triazole compound in mixture of dichloromethane/alcohol preferably a mixture of dichloromethane/straight-chain alcohol and more preferably a mixture of dichloromethane/ethanol whereby the ratio of the fluids is in the range of 30-50/30-50 V/V or most preferably of 50/50 V/V or about 50/50V; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

In another embodiment of the present invention concerns a method of preparation of a solid dispersion of a triazole compound such as 1) Itraconazole, 2) an Itraconazole derivative, 3) a triazole compound wherein the polar surface area (PSA) is in the range from 60 Å2 to 200 Å2, preferably from 70 Å2 to 160 Å2, more preferably form 80 Å2 to 140 Å2, yet more preferably from 90 Å2 to 120 Å2, and most preferably from 95 Å2 to 110 Å2, 4) a triazole compound with a partition coefficient (X log P) in the range from 4 to 9, more preferably in the range from 5 to 8 and most preferably in the range from 6 to 7, 5) a triazole compound with more than 10 freely rotating bonds, 6) triazole compound with polar surface area (PSA) in the range from 80 and 200, a partition coefficient in the range from 3 and 8 and with 8 to 16 freely rotating bonds or 7) a triazole compound with a Polar Surface Area lager than 80 Å. with a polyvinyl alcohol-polyethylene glycol graft copolymer (PVA-PEG graft co-polymer), such as Kollicoat IR whereby the method comprises a) dissolving the polyvinyl alcohol-polyethylene glycol graft copolymer (PVA-PEG graft co-polymer), such as Kollicoat IR, separately in a water/alcohol mixture preferably a mixture of a straight-chain alcohol with water or a mixture of ethanol with water; and b) dissolving the triazole compound in mixture of a alcohol with a non alcoholic organic solvent in which the triazole compound has an high solubility with, preferably a mixture of a straight-chain alcohol with the organic solvent or most preferably a mixture of ethanol with the organic solvent; and c) mixing the both solutions to obtain a total amount of solved solid of 1 to 15 g per 100 ml, preferably 2 to 10 g per 100 ml, yet more preferably 3 to 7 g per 100 ml and most about 5 g per 100 mL and optionally having an acid in the mixture of both the solutions to achieve an acid pH for instance a pH lower than 3 e.g. by adding the acid to the mixture or optionally having a base in the mixture of both the solutions to achieve a basic pH for instance above 10 e.g. by adding the base to the mixture; and d) spray drying such solution.

Solvent Systems for Use in a Method of Preparation of a Solid Dispersion of a Water-soluble Polymer with a Bioactive Compound In step (a) of a method, according to the present invention, a water-soluble polymer, preferably a polyvinyl alcohol-polyethylene glycol graft copolymer, is dissolved in water or a mixture comprising water and at least one first alcohol to form a first solution.

In step (a) of an alternative embodiment of the method, according to the present invention, a polyvinyl alcohol-polyethylene glycol graft copolymer (PVA-PEG graft co-polymer), such as Kollicoat IR, is dissolved in a water/first alcohol mixture.

The at least one first alcohol used in step a) is preferably a straight-chain alcohol. such as ethanol.

The at least one first alcohol used in step a) is particularly preferably selected from the group consisting of ethanol, n-butanol ($CH_3-CH_2-CH_2-CH_2-OH$), isopropanol, ($CH_3-CH(-OH)-CH_3$), n-propanol ($CH_3-CH_2-CH_2-OH$), methanol ($CH_3-OH$) or mixtures thereof, with ethanol being particularly preferred.

The ratio of water to alcohol in step a) is preferably in the range 30/50 to 50/30 v/v. In step (b) of a method, according to the present invention, at least one bioactive compound, such as a BCS class II drug or a BCS class IV drug, is dissolved in a mixture comprising at least one second alcohol and at least one non-alcoholic organic solvent to form a second solution.

In step (b) of an alternative embodiment of the method, according to the present invention, at least one bioactive compound, such as a BCS Class II drug or a BCS Class IV drug, is dissolved in a mixture of a second alcohol with a non alcoholic organic solvent in which the compound has a high solubility.

In step (b) the bioactive compound is preferably dissolved in an organic (carbon-containing) solvent such as dichloromethane and a straight-chain alcohol such as ethanol.

The at least one second alcohol used in step b) is preferably selected from the group consisting of ethanol, n-butanol ($CH_3-CH_2-CH_2-CH_2-OH$), isopropanol, ($CH_3-CH(-OH)-CH_3$), n-propanol ($CH_3-CH_2-CH_2-OH$), methanol ($CH_3-OH$), 2-propanol and hexafluoro-isopropanol, or mixtures thereof, with ethanol being particularly preferred.

The at least one first alcohol is preferably the same as the at least one second alcohol.

The at least one non-alcoholic organic solvent used in step b) is preferably selected from the group consisting of halogenated hydrocarbons, ether, aliphatic hydrocarbons, aromatic hydrocarbons, polar aprotic solvents and organic acids, or dichloromethane, 1,4-dioxane, tetrahydrofuran, N-methyl-pyrroldinon, chloroform, acetone, acetonitrile, dimethylformamide, dimethylsulfoxide, hexane, benzene, toluene, diethyl ether and ethyl acetate, with dichloromethane being particularly preferred. The organic (carbon-containing) solvent is preferably dichloromethane ($CH_2Cl_2$) or other reaction inert solvents such as 1,4-dioxane, tetrahydrofuran, 2-propanol, N-methyl-pyrrolidinon, chloroform, hexafluoroisopropanol and the like. Particularly suitable alternative solvents for dichloromethane are the polar aprotic solvents selected from the group 1,4-Dioxane (/—$CH_2$—$CH_2$—O—$CH_2$—$CH_2$—O—\), tetrahydrofuran (/—$CH_2$—$CH_2$—O—$CH_2$—$CH_2$—\), acetone ($CH_3$—C(=O)—$CH_3$), acetonitrile ($CH_3$—C≡N), dimethylformamide (H—C(=O)N($CH_3$)$_2$) or dimethyl sulfoxide ($CH_3$—S(=O)—$CH_3$) or members selected of the group of the non-polar solvents such as hexane ($CH_3$—$CH_2$—$CH_2$—$CH_2$—$CH_2$—$CH_3$), benzene ($C_6H_6$), toluene ($C_6H_5$—$CH_3$), diethyl ether ($CH_3CH_2$—O—$CH_2$—$CH_3$), chloroform ($CHCl_3$), ethyl acetate ($CH_3$—C(=O)O—$CH_2$—$CH_3$). Moreover appropriate organic (carbon-containing) solvent for the meaning of this invention is a solvent in which the poorly water soluble bioactive species or drug is soluble or which is an organic solvent in which a poorly water soluble drug has high solubility. For instance an organic compound such as a fluorinated alcohol for instance hexafluoroisopropanol, (HFIP-($CF_3$)$_2$CHOH) exhibits strong hydrogen bonding properties can be used to dissolve substances that serve as hydrogen-bond acceptors, such as amides and ethers, which are poorly water soluble. Bioactive species or drug compounds of the amides class contain carbonyl (C=O) and ether (N—C) dipoles arising from covalent bonding between electronegative oxygen and nitrogen atoms and electro-neutral carbon atoms, whereas the primary and secondary amides also contain two- and one N—H dipoles, respectively. The presence of a C=O dipole and, to a lesser extent a N—C dipole, allows amides to act as H-bond acceptors, which makes that HFIP is an appropriate solvent. For instance another group of organic solvent are the non-polar solvents for instance halogenated hydrocarbons (e.g. dichloromethane, chloroform, chloroethane, trichloroethane, carbon tetrachloride, etc.), where under the most preferred is dichloromethane (DCM) or methylene chloride, which is an appropriate solvent for bioactive species or drugs such as diazepam, alpha-methyl-p-tyrosine, phencyclidine, quinolinic acid, simvastatin, lovastatin; paclitaxel, alkaloids, cannabinoids. Files and databases are available for common solvents and drug compounds [such as COSMOfiles (Trademark) of Cosmologic Gmbh & Co, GK] to the skilled man to select an appropriate solvent to load the know poorly soluble biologically active species into the ordered mesoporous oxides. For new structures drug solubility in any solvent can be calculated using thermodynamic criteria which contain basic physical properties and phase equilibrium relationships for instance by computational chemistry and fluid dynamics expert systems (T. Bieker, K. H. Simmrock, Comput. Chem. Eng. 18 (Suppl. 1) (1993) S25-S29; K. G. Joback, G. Stephanopoulos, Adv. Chem. Eng. 21 (1995) 257-311; L. Constantinou, K. Bagherpour, R. Gani, J. A. Klein, D. T. Wu, Comput. Chem. Eng. 20 (1996) 685-702; J. Gmehling, C. Moellmann, Ind. Eng. Chem. Res. 37 (1998) 3112-3123; M. Hostrup, P. M. Harper, R. Gani, Comput. Chem. Eng. 23 (1999) 1395-1414 and R. Zhao, H. Cabezas, S. R. Nishtala, Green Chemical Syntheses and Processes, ACS Symposium Series 767, American Chemical Society, Washington, D.C., 2000, pp. 230-243.) such as COSMOfrag/COSMOtherm (Trademark) of Cosmologic Gmbh & Co, GK, which interact with databases of multiple characterized molecules. Another opportunity is the availability to the skilled person of the automated drug solubility testers such as the Biomek® FX of Millipore to test without undue burden the water solubility of selected compound.

In another embodiment the non-alcoholic solvent in step b) is an organic acid such as acetic acid, propanoic acid, hydroxyacetic acid, lactic acid, pyruvic acid, oxalic acid, malonic acid, succinic acid, maleic acid, fumaric acid, malic acid, tartaric acid, citric acid, methane-sulfonic acid, ethanesulfonic acid, benzenesulfonic acid, p-toluenesulfonic acid, cyclamic acid, salicylic acid, p-aminosalicylic acid and palmoic acid.

The ratio of at least one second alcohol to non-alcoholic solvent in step b) is preferably in the range 30/50 to 50/30 v/v.

The mixture of the first and second solutions is preferably a third solution.

The mixing time of the first and second solution in step (c) of the method, according to the present invention, is preferably carried out for 1 to 30 minutes.

Preferably the concentration of the BCS class II drug or BCS class IV drug in the mixture of the first and second solutions or the third solution is in the range between 0.1 to 150 mg/ml, with 2 to 10 g per 100 ml being preferred, 3 to 7 g per 100 ml being particularly preferred and at most about 5 g per 100 mL being especially preferred.

Preferably the concentration of bioactive compound in the mixture of the first and second solutions or the third solution is in the range between 2 to 10 g per 100 ml, with 3 to 7 g per 100 ml being preferred and at most about 5 g per 100 mL being particularly preferred.

Acids

An acid can be optionally added to the first solution, the second solution or the mixture of the first and second solutions (third solution) in the process according to the present invention. The optionally added acid is an inorganic or organic acid. Addition of an inorganic acid to the first solution in the process according to the present invention is preferred, with addition of hydrochloric acid being particularly preferred.

In a further embodiment an acid is preferably added to the second solution in step b). More preferably at least one inorganic acid or at least one organic acid selected from the group consisting of hydrochloric acid, hydrobromic acid, sulfuric acid, nitric acid, phosphoric acid, acetic acid, propanoic acid, hydroxyacetic acid, pyruvic acid, oxalic acid, malonic acid, succinic acid, maleic acid, fumaric acid, malic acid, tartaric acid, citric acid, methane-sulfonic acid, ethanesulfonic acid, benzenesulfonic acid, p-toluenesulfonic acid, cyclamic acid, salicylic acid, p-aminosalicylic acid and palmoic acid is added to the second solution in step b).

The added inorganic acid is preferably selected from the group consisting of hydrohalic acids e.g. hydrochloric or hydrobromic acid; sulfuric acid; nitric acid; phosphoric acid and the like acids. The added organic acid is preferably selected from the group consisting of acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, palmoic and the like acids. A specific acid can be selected based on de pKa of a compound.

The addition of hydrochloric acid is particularly preferred.

In another embodiment an acid is preferably added to the mixture of the first and second solutions is preferred to achieve an acid pH, with acids, including inorganic acids including hydrohalic acids, e.g. hydrochloric or hydrobromic acid; sulfuric; nitric; phosphoric and the like acids; or organic acids including acetic, propanoic, hydroxyacetic, lactic, pyruvic, oxalic, malonic, succinic, maleic, fumaric, malic, tartaric, citric, methane-sulfonic, ethanesulfonic, benzene-sulfonic, p-toluenesulfonic, cyclamic, salicylic, p-aminosalicylic, palmoic and the like acids.

Bases

A base can be optionally to the first solution, second solution or the mixture of the first and the second solutions (third solution) in the process, according to the present invention.

A base is preferably added to the second solution in step b), the added base being preferably selected from the group consisting of sodium hydroxide, sodium hydride, potassium hydroxide, pyridine, morpholine, N-methyl-morpholine, triethylamine, N,N-di-isopropyl-ethylamine, dimethylamine.

The added base is particularly preferably selected from the group consisting of sodium hydroxide, sodium hydride, triethylamine, N,N-di-isopropyl-ethylamine and the like.

Bioactive Compound

The bioactive compound used in the method, according to the present invention, preferably has a polar surface area (PSA) in the range from 70 $Å^2$ to 160 $Å^2$, with from 80 $Å^2$ to 140 $Å^2$ being particularly preferred, 90 $Å^2$ to 120 $Å^2$ being especially preferred and 95 $Å^2$ to 110 $Å^2$ being especially particularly preferred.

The bioactive compound used in the method, according to the present invention, preferably has a partition coefficient (X log P) in the range 5 to 8, with the range 6 to 7 being particularly preferred.

Drugs

The Biopharmaceutical Classification System (BCS) is a framework for classifying drug substances based on their aqueous solubility and intestinal permeability (Amidon, G. L., Lennernas H., Shah V. P., and Crison J. R., "A Theoretical Basis For a Biopharmaceutics Drug Classification: The Correlation of In Vitro Drug Product Dissolution and In Vivo Bioavailability", Pharmaceutical Research, 12: 413-420 (1995) and Adkin, D. A., Davis, S. S., Sparrow, R. A., Huckle, P. D. and Wilding, I. R., 1995. The effect of mannitol on the oral bioavailability of cimetidine. J. Pharm. Sci. 84, pp. 1405-1409).

The Biopharmaceutical Classification System (BCS), originally developed by G. Amidon, separates pharmaceuticals for oral administration into four classes depending on their aqueous solubility and their permeability through the intestinal cell layer. According to the BCS, drug substances are classified as follows:
Class I—High Permeability, High Solubility
Class II—High Permeability, Low Solubility
Class III—Low Permeability, High Solubility
Class IV—Low Permeability, Low Solubility The interest in this classification system stems largely from its application in early drug development and then in the management of product change through its life-cycle. In the early stages of drug development, knowledge of the class of a particular drug is an important factor influencing the decision to continue or stop its development. The present delivery form and the suitable method of present invention can change this decision point by providing better bioavailability of Class 2 drugs of the BCS system.

The solubility class boundary is based on the highest dose strength of an immediate release ("IR") formulation and a pH-solubility profile of the test drug in aqueous media with a pH range of 1 to 7.5. Solubility can be measured by the shake-flask or titration method or analysis by a validated stability-indicating assay. A drug substance is considered highly soluble when the highest dose strength is soluble in 250 ml or less of aqueous media over the pH range of 1-7.5. The volume estimate of 250 ml is derived from typical bioequivalence (BE) study protocols that prescribe administration of a drug product to fasting human volunteers with a glass (about 8 ounces) of water. The permeability class boundary is based, directly, on measurements of the rate of mass transfer across human intestinal membrane, and, indirectly, on the extent of absorption (fraction of dose absorbed, not systemic bioavailability) of a drug substance in humans. The extent of absorption in humans is measured using mass-balance pharmacokinetic studies; absolute bioavailability studies; intestinal permeability methods; in vivo intestinal perfusion studies in humans; and in vivo or in situ intestinal perfusion studies in animals. In vitro permeation experiments can be conducted using excised human or animal intestinal tissue and in vitro permeation experiments can be conducted with epithelial cell monolayers. Alternatively, nonhuman systems capable of predicting the extent of drug absorption in humans can be used (e.g., in vitro epithelial cell culture methods). In the absence of evidence suggesting instability in the gastrointestinal tract, a drug is considered highly soluble when 90% or more of an administered dose, based on a mass determination or in comparison to an intravenous reference dose, is dissolved. 'FDA 'guidance states pH 7.5, ICH/EU guidance states pH 6.8. An immediate release drug product is considered rapidly dissolving when no less than 85% of the labelled amount of the drug substance dissolves within 30 minutes, using USP Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes. Based on the BCS, low-solubility compounds are compounds whose highest dose is not soluble in 250 mL or less of aqueous media from pH 1.2 to 7.5 at 37° C. See Cynthia K. Brown, et al., "Acceptable Analytical: Practices for Dissolution Testing of Poorly Soluble Compounds", Pharmaceutical Technology (December 2004). An immediate release (IR) drug product is considered rapidly dissolving when no less than 85% of the labeled amount of the drug substance dissolves within 30 minutes, using U.S. Pharmacopeia (USP) Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes.

A drug substance is considered highly permeable when the extent of absorption in humans is determined to be greater than 90% of an administered dose, based on mass-balance or in comparison to an intravenous reference dose. The permeability class boundary is based, directly, on measurements of the rate of mass transfer across human intestinal membrane, and, indirectly, on the extent of absorption (fraction of dose absorbed, not systemic bioavailability) of a drug substance in humans. The extent of absorption in humans is measured using mass-balance pharmacokinetic studies; absolute bioavailability studies; intestinal permeability methods; in viva intestinal perfusion studies in humans; and in vivo or in situ intestinal perfusion studies in animals. In vitro permeation experiments can be conducted using excised human or animal intestinal tissue and in vitro permeation experiments can be conducted with epithelial cell monolayers. i Alternatively, nonhuman systems capable of predicting the extent of drug I absorption in humans can be used (e.g., in vitro epithelial cell culture methods). A drug substance is considered highly permeable when the extent of absorption in humans is determined to be greater than 90% of an I administered dose, based on mass-balance or in comparison to an intravenous reference dose. A drug substance is considered to have low permeability when the extent of absorption in humans is determined to be less than 90% of an administered dose, based on mass-balance or in comparison to an intravenous reference dose. An IR drug product is considered rapidly dissolving when no less than 85% of the labeled amount of the drug substance dissolves within 30 minutes, using U.S. Pharmacopeia (USP) Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes.

BCS Class II Drugs are drugs that are particularly insoluble, or slow to dissolve, but that readily are absorbed from solution by the lining of the stomach and/or the intestine. Hence, prolonged exposure to the lining of the GI tract is required to achieve absorption. Such drugs are found in many therapeutic classes. Class II drugs are particularly insoluble or slow to dissolve, but readily are absorbed from solution by the lining of the stomach and/or the intestine. Prolonged exposure to the lining of the GI tract is required to achieve absorption. Such drugs are found in many therapeutic classes. A class of particular interest is antifungal agents, such as itraconazole. Many of the known Class II drugs are hydrophobic, and have historically been difficult to administer. Moreover, because of the hydrophobicity, there tends to be a significant variation in absorption depending on whether the patient is fed or fasted at the time of taking the drug. This in turn can affect the peak level of serum concentration, making calculation of dosage and dosing regimens more complex. Many of these drugs are also relatively inexpensive, so that simple formulation methods are required and some inefficiency in yield is acceptable.

In a preferred embodiment of the present invention the bioactive compound is a BCS class II drug selected from the group consisting of itraconazole, fluconazole, terconazole, ketoconazole, saperconazole, sulfasalazine, griseofulvin, griseoverdin, atovaquone, cyclosporine, digoxin, spironolactone, ibuprofen, ritonavir, nevirapine, lopinavir, clofazinine, diloxanide furoate, glibenclamide, nefidepine, danazol, carbamazepine and acyclovir.

In a particularly preferred embodiment of present invention the BCS class II drug is intraconazole or a related drug, such as fluoconazole, terconazole, ketoconazole, and saperconazole.

In an especially preferred embodiment the BCS class II drug is selected from the group consisting of itraconazole and cyclosporine.

Itraconazole is a Class II medicine used to treat fungal infections and is effective against a broad spetrum of fungi including dermatophytes (tinea infections), *candida*, *malassezia*, and chromoblastomycosis. Itraconazole works by destroying the cell wall and critical enzymes of yeast and other fungal infectious agents. Itraconazole can also decrease testosterone levels, which makes it useful in treating prostate cancer and can reduce the production of excessive adrenal corticosteroid hormones, which makes it i useful for Cushing's syndrome. Itraconazole is available in capsule and oral I solution form. For fungal infections the recommended dosage of oral capsules is 200-400 mg once a day.

Itraconazole has been available in capsule form since 1992, in oral I solution form since 1997, and in an intravenous formulation since 1999. Since Itraconazole is a highly lipophilic compound, it achieves high concentrations in fatty tissues and purulent exudates. However, its penetration into aqueous fluids is very limited. Gastric acidity and food heavily influence the absorption of the oral formulation (Bailey, et al., Pharmacotherapy, 10: 146-153 (1990)). The absorption of itraconazole oral capsule is variable and unpredictable, despite having a bioavailability of 55%.

Other suitable drugs include Class II anti-infective drugs, such as griseofulvin and related compounds such as griseoverdin; some anti malaria drugs (e.g Atovaquone); immune system modulators (e.g cyclosporine); and cardiovascular drugs (e.g. digoxin and spironolactone); and ibuprofen. In addition, sterols or steroids may be used. Drugs such as Danazol, carbamazopine, and acyclovir may also be used in the compositions.

Danazol is derived from ethisterone and is a synthetic steroid. Danazol is designated as 17a-Pregna-2,4-dien-20-yno[2,3-d]-isoxazol-17-ol, has the formula of $C_{22}H_{27}NO_2$, and a molecular weight of 337.46. Danazol is a synthetic steroid hormone resembling a group of natural hormones (androgens) that are found in the body. Danazol is used in the treatment of endometriosis. It is also useful in the treatement of fibrocystic breast disease and hereditary angioedema. Danazol works to reduce estrogen levels by inhibiting the production of hormones called gonadotrophins by the pituitary gland. Gonadotrophins normally stimulate the production of sex hormones such as estrogen and progestogen, which are responsible for body processes such as menstruation and ovulation. Danazol is administered orally, has a bioavailability that is not directly dose-related, and a half-life of 4-5 hours. Dosage increases in danazol are not proportional to increases in plasma concentrations. It has been shown that doubling the dose may yield only a 30-40% increase in I plasma concentration. Danazol peak concentrations occur within 2 hours, but the therapeutic effect usually does not occur for approximately 6-8 weeks I after taking daily doses.

Acyclovir is a synthetic nucleoside analogue that acts as an antiviral agent. Acyclovir is available for oral administration in capsule, tablet' and suspension forms. It is a white, crystalline powder designated as 2-amino-1,9-dihydro-9-[(2-hydroxyethoxy)methyl]-6H-purin-6-one, has an empirical formula of $C_8H_{11}N_5O_3$ and a molecular weight of 225.

Acyclovir has an absolute bioavailability of 20% at a 200 mg dose given every 4 hours, with a half-life of 2.5 to 3.3 hours. In addition, the bioavailability decreases with increasing doses. Despite its low bioavailability, acyclovir is highly specific in its inhibitory activity of viruses due to its high affinity for thymidine kinase (TK) (encoded by the virus). TK converts acyclovir into a nucleotide analogue which prevents replication of viral DNA by inhibition and/or inactivation of the viral DNA polymerase, and through termination of the growing viral DNA chain.

Carbamazepine is used in the treatment of psychomotor epilepsy, and as an adjunct in the treatment of partial epilepsies. It can also relieve or diminish pain that is associated with trigeminal neuralgia. Carbamazepine given as a monotherapy or in combination with lithium or neuroleptics has also been found useful in the treatment of acute mania and the prophylactic treatment of bipolar disorders.

Carbamazepine is a white to off-white powder, is designated as 5H dibenz[b,f]azepine-5-carboxamide, and has a molecular weight of 236.77. It is practically insoluble in water and soluble in alcohol and acetone. The absorption of Carbamazepine is relatively slow, despite a bioavailability of 89% for the tablet form. When taken in a single oral dose, the Carbamazepine tablets and chewable tablets yield peak plasma concentrations of unchanged Carbamazepine within 4 to 24 hours. The therapeutic range for the steady-state plasma concentration of Carbamazepine generally lies between 4 and 10 mcg/mL. Other representative Class II compounds are antibiotics to kill *Helicobacter pylori* include amoxicillin, tetracyline and metronidazole or therapeutic agents including acid suppressants (H2 blockers include cimetidine, ranitidine, famotidine, and nizatidine; Proton pump inhibitors include omeprazole, lansoprazole, rabeprazole, esomeprazole, and pantoprozole), mucosal defense enhancing agent (bismuth salts; bismuth subsalicylate) and/or mucolytic agents (megaldrate).

Many of the known Class II drugs are hydrophobic, and have historically been difficult to administer. Moreover, because of the hydrophobicity, there tends to be a significant variation in absorption depending on whether the patient is fed or fasted at the time of taking the drug. This in turn can affect the peak level of serum concentration, making calculation of dosage and dosing regimens more complex. Many of these drugs are also relatively inexpensive, so that simple formulation methods are required and some inefficiency in yield is acceptable.

In a preferred embodiment of present invention, the drug is intraconazole and its relatives fluoconazole, terconazole, ketoconazole, and saperconazole. Itraconazole is a Class II medicine used to treat fungal infections and is effective against a broad spetrum of fungi including dermatophytes (tinea infections), *candida, malassezia*, and chromoblastomycosis. Itraconazole works by destroying the cell wall and critical enzymes of yeast and other fungal infectious agents. Itraconazole can also decrease testosterone levels, which makes it useful in treating prostate cancer and can reduce the production of excessive adrenal corticosteroid hormones, which makes it useful for Cushing's syndrome. Itraconazole is available in capsule and oral solution form. For fungal infections the recommended dosage of oral capsules is 200-400 mg once a day.

Itraconazole has been available in capsule form since 1992, in oral solution form since 1997, and in an intravenous formulation since 1999. Since itraconazole is a highly lipophilic compound, it achieves high concentrations in fatty tissues and purulent exudates. However, its penetration into aqueous fluids is very limited. Gastric acidity and food heavily influence the absorption of the oral formulation (Bailey, et al., Pharmacotherapy, 10: 146-153 (1990)). The absorption of itraconazole oral capsule is variable and unpredictable, despite having a bioavailability of 55%.

Other Class II drugs include anti-infective drugs such as sulfasalazine, griseofulvin and related compounds such as griseoverdin; some anti malaria drugs (e.g. Atovaquone); immune system modulators (e.g. cyclosporine); and cardiovascular drugs (e.g. digoxin and spironolactone); and ibuprofen (analgesic); ritonavir, nevirapine, lopinavir (antiviral); clofazinine (leprostatic); diloxanide furoate (anti-amebic); glibenclamide (anti-diabetes); nifedipine (anti-anginal); spironolactone (diuretic); steroidal drugs such as Danazol; carbamazepine, and anti-virals such as acyclovir.

Danazol is derived from ethisterone and is a synthetic steroid. Danazol is designated as 17a-Pregna-2,4-dien-20-yno[2,3-d]-isoxazol-17-ol, has the formula of C22H27NO2, and a molecular weight of 337.46. Danazol is used in the treatment of endometriosis, fibrocystic breast disease and hereditary angioedema. Danazol is administered orally, has a bioavailability that is not directly dose-related, and a half-life of 4-5 hours. Dosage increases in danazol are not proportional to increases in plasma concentrations. It has been shown that doubling the dose may yield only a 30-40% increase in plasma concentration. Danazol peak concentrations occur within 2 hours, but the therapeutic effect usually does not occur for approximately 6-8 weeks after taking daily doses.

Acyclovir is a synthetic nucleoside analogue that acts as an antiviral agent. Acyclovir is available for oral administration in capsule, tablet, and suspension forms. It is a white, crystalline powder designated as 2-amino-1,9-dihydro-9-[(2-hydroxyethoxy)methyl]-6H-purin-6-one, has an empirical formula of C8H11N5O3 and a molecular weight of 225. Acyclovir has an absolute bioavailability of 20% at a 200 mg dose given every 4 hours, with a half-life of 2.5 to 3.3 hours. The bioavailability decreases with increasing doses. Despite its low bioavailability, acyclovir is highly specific in its inhibitory activity of viruses due to its high affinity for thymidine kinase (TK) (encoded by the virus). TK converts acyclovir into a nucleotide analogue which prevents replication of viral DNA by inhibition and/or inactivation of the viral DNA polymerase, and through termination of the growing viral DNA chain.

Carbamazepine is used in the treatment of psychomotor epilepsy, and as an adjunct in the treatment of partial epilepsies. It can also relieve or diminish pain that is associated with trigeminal neuralgia. Carbamazepine given as a monotherapy or in combination with lithium or neuroleptics has also been found useful in the treatment of acute mania and the prophylactic treatment of bipolar disorders. Carbamazepine is a white to off-white powder, is designated as 5H-dibenz[b,f]azepine-5-carboxamide, and has a molecular weight of 236.77. It is practically insoluble in water and soluble in alcohol and acetone. The absorption of carbamazepine is relatively slow, despite a bioavailability of 89% for the tablet form. When taken in a single oral dose, the carbamazepine tablets and chewable tablets yield peak plasma concentrations of unchanged carbamazepine within 4 to 24 hours. The therapeutic range for the steady-state plasma concentration of carbamazepine generally lies between 4 and 10 mcg/mL BCS Class IV Drugs (Low Permeability, Low Solubility) are drugs that are particularly insoluble, or slow to dissolve, in water and with poor GI permeability.

Most class IV drugs are lipophilic drugs which results in their consequent poor GI permeability. Examples include acetazolamide, furosemide, tobramycin, cefuroxmine, allopurinol, dapsone, doxycycline, paracetamol, nalidixic acid, clorothiazide, tobramycin, cyclosporin, tacrolimus, and paclitaxel. Tacrolimus is a macrolide immunosuppressant produced by *Streptomyces tsukubaensis*. Tacrolimus prolongs the survival of the host and transplanted graft in animal transplant models of liver, kidney, heart, bone marrow, small bowel and pancreas, lung and trachea, skin, cornea, and limb. Tacrolimus acts as an immunosuppressant through inhibition of T-lymphocyte activation through a mechanism that is unknown. Tacrolimus has an empirical formula of $C_{44}H_{69}NO$ $12.H_2O$ and a formula weight of 822.05. Tacrolimus appears as white crystals or crystalline powder. It is practically insoluble in water, freely soluble in ethanol, and very soluble in methanol and chloroform. Tacrolimus is available for oral administration as capsules or as a sterile solution for injection. Absorption of tacrolimus from the gastro-intestinal tract after oral administration is incomplete and variable. The absolute bioavailability of tacrolimus is approximately 17% at a 5 mg dose taken twice a day. Paclitaxel is a chemotherapeutic agent that displays cytotoxic and antitumor activity. Paclitaxel is a natural product obtained via a semi-synthetic process from *Taxus baccata*. While having an unambiguous reputation of tremendous therapeutic potential, paclitaxel has some patient-related drawbacks as a therapeutic agent. These partly stem from its extremely low solubility in water, which makes it difficult to provide in suitable dosage form. Because of paclitaxels poor aqueous solubility, the current approved (U.S. FDA) clinical formulation consists of a 6 mg/ml solution of paclitaxel in 50% polyoxyethylated castor oil (CREMOPHOR EL®) and 50% dehydrated alcohol. Am. J. Hosp. Pharm., 48:1520-24 (1991). In some instances, severe reactions, including hypersensitivity, occur in conjunction with the CREMOPHOR® administered in conjunction with paclitaxel to compensate for its low water solubility. As a result of the incidence of hypersensitivity reactions to the commercial paclitaxel formulations and the potential for paclitaxel precipitation in the blood, the formulation must be infused over several hours. In addition, patients must be pretreated with steroids and antihistamines prior to the infusion. Paclitaxel is a white to off-white crystalline powder available in a non-aqueous solution for injection. Paclitaxel is highly lipophilic and insoluble in water.

In a preferred embodiment of the present invention the bioactive compound is a BCS class IV drug selected from the group consisting of acetazolamide, furosemide, tobramycin, cefuroxmine, allopurinol, dapsone, doxycycline, paracetamol, nalidixic acid, clorothiazide, tobramycin, cyclosporin, tacrolimus, paclitaxel, prostaglandines, including prostaglandine E2, prostaglandine F2 and prostaglandine E1, proteinase inhibitors including indinavire, nelfinavire, saquinavir, cytotoxics, including, doxorubicine, daunorubicine, epirubicine, idarubicine, zorubicine, mitoxantrone, amsacrine, vinblastine, vincristine, vindesine, dactiomycine, bleomycine, metallocenes, including titanium metallocene dichloride, and lipid-drug conjugates, including diminazene stearate and diminazene oleate, chloroquine, mefloquine, primaquine, vancomycin, vecuronium, pentamidine, metronidazole, nimorazole, tinidazole, atovaquone and buparvaquone.

Examples of compounds that are poorly soluble in water are poorly soluble drugs can be taken from the groups of the prostaglandines, e.g. prostaglandine E2, prostaglandine F2 and prostaglandine E1, proteinase inhibitors, e.g. indinavire, nelfinavire, ritonavire, saquinavir, cytotoxics, e.g. paclitaxel, doxorubicine, daunorubicine, epirubicine, idarubicine, zorubicine, mitoxantrone, amsacrine, vinblastine, vincristine, vindesine, dactiomycine, bleomycine, metallocenes, e.g. titanium metallocene dichloride, and lipid-drug conjugates, e.g. diminazene stearate and diminazene oleate, and generally poorly insoluble anti-infectives such as griseofulvine, ketoconazole, fluconazole, itraconazole, clindamycine, especially antiparasitic drugs, e.g chloroquine, mefloquine, primaquine, vancomycin, vecuronium, pentamidine, metronidazole, nimorazole, tinidazole, atovaquone, buparvaquone, nifurtimoxe and anti-inflammatory drugs, e.g. cyclosporine, methotrexate, azathioprine.

The present invention concerns in an embodiment 1) Itraconazole, 2) an Itraconazole derivative, 3) a triazole compound wherein the polar surface area (PSA) is in the range from 60 Å2 to 200 Å2, preferably from 70 Å2 to 160 Å2, more preferably form 80 Å2 to 140 Å2, yet more preferably from 90 Å2 to 120 Å2, and most preferably from 95 Å2 to 110 Å2, 4) a triazole compound with a partition coefficient (X log P) in the range from 4 to 9, more preferably in the range from 5 to 8 and most preferably in the range from 6 to 7, 5) a triazole compound with more than 10 freely rotating bonds, 6) triazole compound with polar surface area (PSA) in the range from 80 and 200, a partition coefficient in the range from 3 and 8 and with 8 to 16 freely rotating bonds or 7) A triazole compound with a Polar Surface Area lager than 80 Å.

EXAMPLES

Materials

Itraconazole was obtained from Janssen Pharmaceutics (Beerse, Belgium) and Kollicoat IR from BASF (Ludwigshafen, Germany).

Evaluation Techniques

X-ray Powder Diffraction:

X-ray powder diffraction was performed at room temperature with an automated X'Pert PRO diffractometer (PANalytical, The Netherlands) in Bragg-Brentano geometry with a flat sample stage spinning with a rotation time of 4 s. X'Pert Data Collector version 2.2c (PANalytical, The Netherlands) was used for data collection. In the incident beam path a 0.04 rad soller slit, a 10 mm mask and a programmable divergence slit were installed. In the diffracted beam path a programmable anti scatter slit and a 0.04 rad soller slit were installed. Cu K$\alpha_1$-radiation ($\lambda$=1.540598 Å) was obtained with a 0.02 mm Ni-filter. The irradiated and observed area was 100 mm$^2$. The irradiated and the observed length was 10 mm The diffracted beams were detected with an X'celerator RTMS detector with an active length of 2.122°. The data were collected in continous mode in the region of 7°≦2θ≦40° with a step size of 0.0021° 2θ and a counting time of 19.7 s. The X-ray tube was set up at a voltage of 45 kV and a current of 40 mA. The diffractograms were analyzed using X'pert Data Viewer version 1.2a.

Analysis of the Itraconazole Content

Approximately 50 mg of the solid dispersions was dissolved in 50 mL dimethylsulfoxide (DMSO) and the itraconazole content was determined with HPLC, as described below, using a series of dilutions of itraconazole in DMSO. The exact contents were used to calculate the total amount of itraconazole in the dissolution experiments. Experiments were done in triplicate.

Dissolution Testing

Dissolution experiments were performed in triplicate on Itraconazole/Kollicoat IR® (w/w) spray dried powders. The tests were performed using the USP 24 method 2 (paddle method) in a Hanson SR8plus dissolution apparatus (Chatsworth, Calif., US). To simulate the dissolution of a weak basic compound in the stomach, 500 mL of simulated gastric fluid without pepsin (SGF$_{sp}$; USP 24) was used as dissolution medium at a temperature of 37° C. and a paddle speed of 100 rpm. Spray dried powders (always containing 100 mg of Itraconazole) were added to the dissolution medium. 5 mL samples were taken and immediately replaced with fresh dissolution medium at 5, 10, 15, 30, 45, 60, 120, 180, and 240 min. These samples were filtered with 0.45 μm Teflon filters (Macherey-Nagel, Düuren, Germany). The first two milliliter were discarded. The remainder was diluted with methanol (½) to avoid precipitation, and analyzed with HPLC, as described below.

HPLC Analysis:

HPLC analysis was performed with a Merck Hitachi pump L7100, an ultraviolet (UV) detector (L7400), an autosampler (L7200) and an interface (D7000; Merck, Darmstadt, Germany). A LiChrospher 100 RP-18 (5 ρm, 12.5×4) (Merck, Darmstadt, Germany) column was used. Acetonitrile/tetrabutyl ammonium hydrogen sulphate 0.01N (55:45, v/v) was used as mobile phase at a flow rate of 1.0 mL/min, all solvents used were HPLC grade. The injection volume was 20 μL, and UV detection was used at a wavelength of 260 nm The retention time for Itraconazole was 4.6 min.

Preparation of Solutions:

Kollicoat IR was added to a 50/50 V/V water/ethanol mixture and the dispersion stirred and heated to 50° C. for 10-15 min to obtain a Kollicoat IR solution. Both acidic and non-acidic solutions were evaluated:

Acidic: the water moiety consists of 1 part demineralized water and 1 part 1N hydrochloric acid, the pH of the resulting water/ethanol solution was 1-2.

Non acidic: no hydrochloric acid was added.

Itraconazole was added to a 50/50 V/V dichloromethane/ethanol solvent mixture and the dispersion sonicated to speed up Itraconazole dissolution. For compositions with a high drug load it was necessary to sonicate the itraconazole solution.

The two binary solvent mixtures, dichloromethane/ethanol and water/ethanol were miscible in a 50/50 V/V ratio due to the presence of ethanol. The two separated solutions were only mixed 2 minutes prior to spray drying. During this period and the spray drying process the solution was stirred. The total amount of solid was 5 g per 100 mL of the mixed water/ethanol/dichloromethane solution i.e. 5% w/V with respect to the sum of the volumes of both solutions (itraconazole in 50/50 V/V dichloromethane/ethanol and Kollicoat IR in 50/50 V/V water/ethanol).

Spray Drying:

The solid dispersions were prepared in a Buchi mini spray dryer B191 (Buchi, Flawil, Switzerland). The inlet temperature was set at 80° C. and the outlet temperature varied from 50 to 35° C. The aspirator was set at 100%, the pump at 45%, the air flow was 800 L/h. All spray dried powders were dried for one week in a vacuum oven at 40° C. prior to analysis and further stored in a dessicator over $P_2O_5$ at 25° C.

A series of solid dispersions with Itraconazole/Kollicoat IR w/w fractions ranging from 10 to 50%, were prepared.

Method 1:

In a first approach a spray nozzle with two separate inlets was used so that the solutions were pumped and atomized separately and droplets could only collide in the drying chamber. The samples were spray dried in a Buchi mini spray dryer B191 (Buchi, Flawil, Switzerland) and the following process parameters were used: the flow rate of both pumps were synchronized at 4 ml/min, the temperature was set at 80° C., the outlet temperature varied from 35 to 50° C., the aspirator was set at 100%, and the pressurized air flow rate at 800 L/h. The powders were dried in a vacuum oven (−0.8 bar) at 40° C. for a period of one week, and stored in a desiccator over $P_2O_5$ at 25° C. Since the spray nozzle had one inlet at the side and one at the top, the inlets were varied for the two solutions in order to investigate both possibilities.

Method 2:

In the second approach the itraconazole in 50/50 V/V dichloromethane/ethanol and Kollicoat IR in 50/50 V/V water/ethanol solutions were prepared separately as described above and mixed prior to spray drying. Instead of a spray nozzle with two inlets a spray nozzle with one single inlet (top) was used. In order to improve the solubility of itraconazole (weak base pKa=4.0) these experiments were repeated with a 50/50 V/V 0.1N HCl/water mixture instead of pure water in the 50/50 V/V water/ethanol phase and the resulting pH of the water phase was around 0.6. The samples were spray dried in a Buchi mini spray dryer B191 (Buchi, Flawil, Switzerland) and the following process parameters were used: the pump was set at 45%, which resulted in a flow rate of ca. 6 ml/min, the temperature was set at 80° C., the outlet temperature varied from 35 to 50° C., the aspirator was set at 100%, and the pressurized air flow rate at 800 L/h. The powders were dried in a vacuum oven (−0.8 bar) at 40° C. for a period of one week, and stored in a desiccator over $P_2O_5$ at 25° C.

Dissolution Profiles

Figure 3:
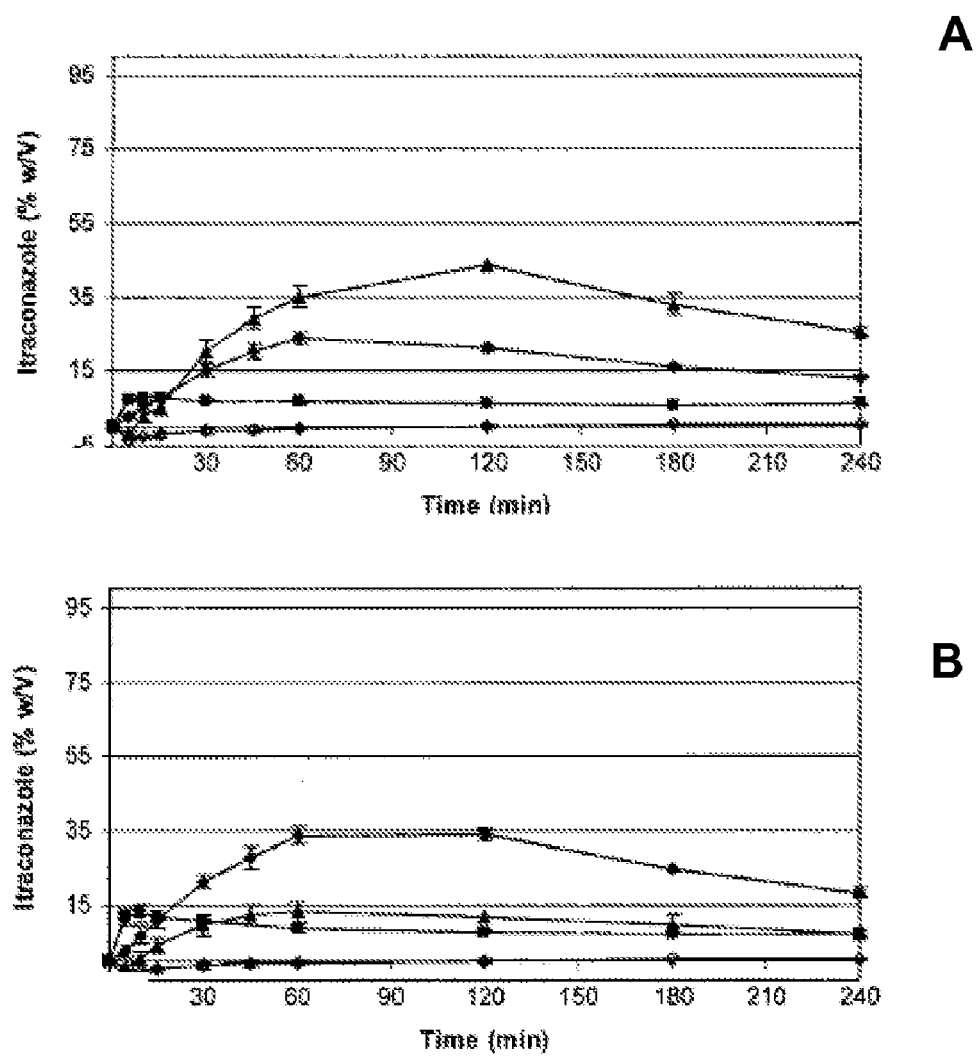
FIG. 3: Dissolution profiles solid dispersions spray dried from two separate solutions using a spray nozzle with two inlets, A: Kollicoat IR from top inlet, itraconazole from side inlet, B: Kollicoat IR from side inlet, itraconazole from top inlet; 10% itraconazole in Kollicoat IR (■), 40% itraconazole in Kollicoat IR (♦), 60% itraconazole in Kollicoat IR (▲), crystalline itraconazole (◇) (n=3, error bars indicate S.D.).

FIG. 3 displays the dissolution profiles of the itraconazole/Kollicoat IR solid dispersions that were prepared according to method 1. All solid dispersions had a better dissolution profile than the pure crystalline drug. However, compared to other itraconazole solid dispersion systems published in literature this result is rather poor. Indeed, a release of 80% for a solid dispersion with a drug load of 20% is not an exception. FIGS. A and B represent the dissolution profiles of the solid dispersions spray dried with itraconazole from the side inlet and Kollicoat IR from the top inlet and visa versa. In FIG. A the extent of dissolution appears to increase with the drug load. In FIG. B on the other hand the solid dispersions with a drug load of 10 and 60% have a similar release where-else the sample with a 40% drug load has a higher release. This means that no trends can be observed with respect to drug-polymer composition and the inlet position of the solutions.

Figure 2:
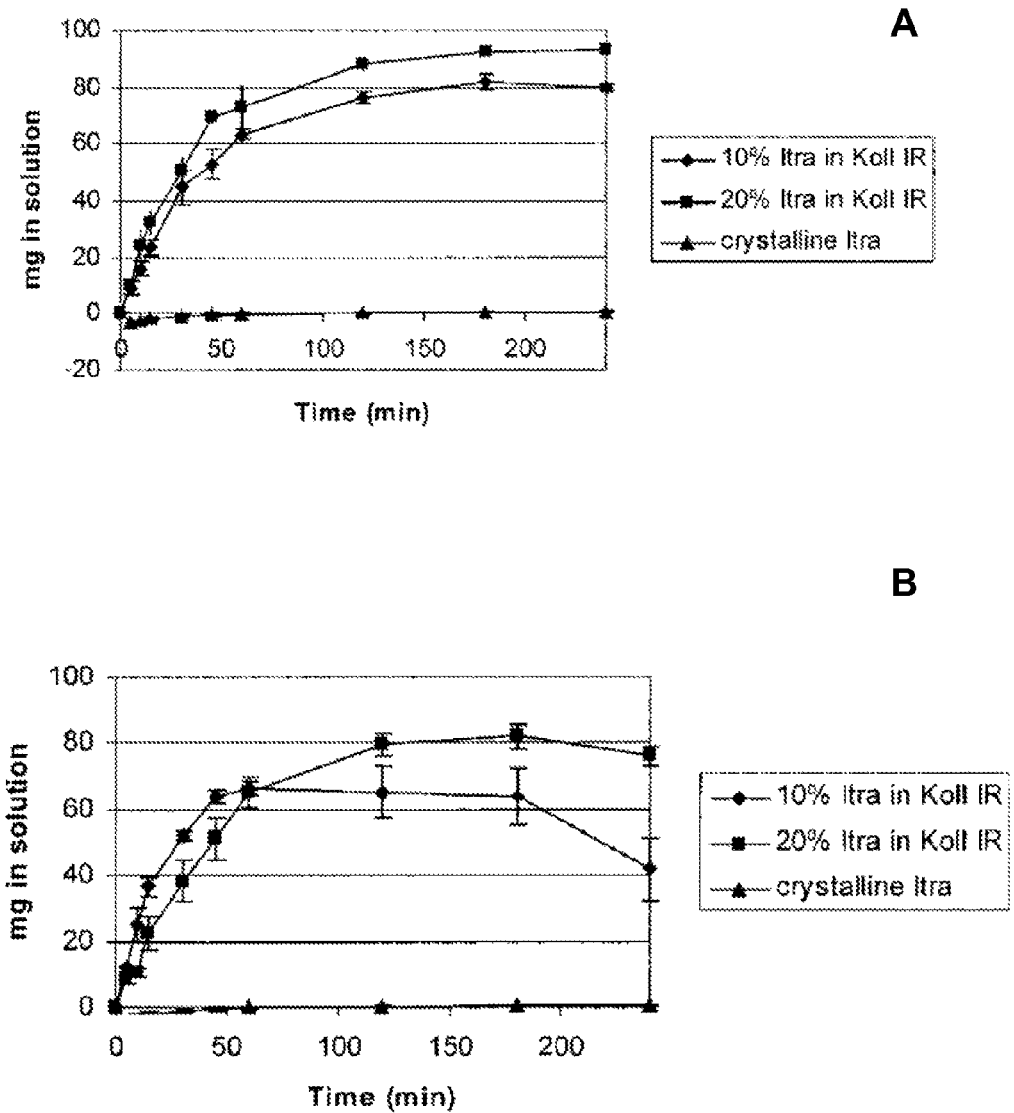
FIG. 2: Dissolution profiles of solid dispersions spray dried from two separate solutions mixed 2 minutes before spray drying for 10% itraconazole and 20% itraconazole: A) with solution 1 having added acid and B) with solution 1 not having added acid with crystalline itraconazole as a reference.

FIG. 2 displays the dissolution profiles of solid dispersions spray dried from two separate solutions mixed 2 minutes before spray drying according to method 2 for 10% and 20% itraconazole: A) with solution 1 having added acid and B) with solution 1 not having added acid with crystalline itraconazole as a reference. FIG. 2 shows the release of itraconazole as mg in solution (500 mL) as a function of time for the four samples and clearly demonstrates a significantly faster release for solid dispersions produced with solution 1 with added hydrochloric acid with both 10% and 20% itraconazole.

Figure 5:
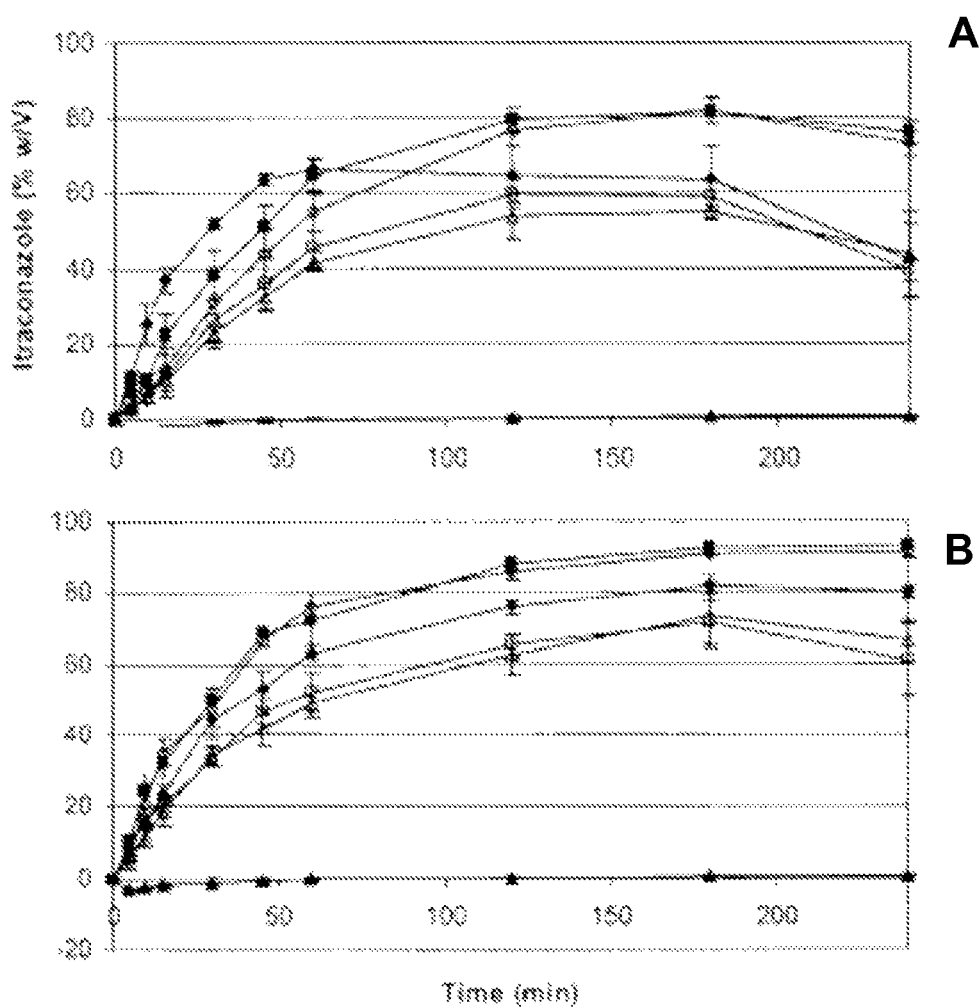
FIG. 5: Dissolution profiles solid dispersions of itraconazole and Kollicoat IR with A representing solid dispersions spray dried from a ternary non acidic solvent, B representing solid dispersions that were spray dried from a ternary acidic solvent; (◆) 10% itraconazole in Kollicoat IR, (■) 20% itraconazole in Kollicoat IR, (◇) 30% itraconazole in Kollicoat IR, (△) 40% itraconazole in Kollicoat IR, (□) 50% itraconazole in Kollicoat IR, (▲) crystalline itraconazole (n=3, error bars indicate S.D.).

FIG. 5 displays the dissolution profiles of both the solid dispersions obtained by spray drying via a spray nozzle with a single inlet according to method 2, in which 5A represents the dissolution profiles of samples that were spray dried from a non acidic ternary solvent and 5B represents the dissolution profiles of samples that were spray dried from an acidic ternary solvent. In both cases a significant improvement was obtained in comparison with the first approach, and the samples that were spray dried from a ternary acidic solution exerted a higher dissolution than the samples that were spray dried from a non acidic solution. For both data series, acidic and non acidic, the best results were obtained for the samples with a drug load of 20 and 30%, followed by the dissolution of the samples containing 10% of itraconazole and finally the samples with a drug load of 40 and 50%. Especially for the samples that were spray dried from an acidic solution it was remarkable that the extent of dissolution was over 90% for a solid dispersion with a drug load of 30%. In comparison with the reported dissolution profiles of co-extruded itraconazole/Kollicoat IR solid dispersions the extent of dissolution is higher for the samples spray dried from the acidic ternary solvent, but the dissolution rate is lower.

X-ray Powder Diffraction

Figure 4:
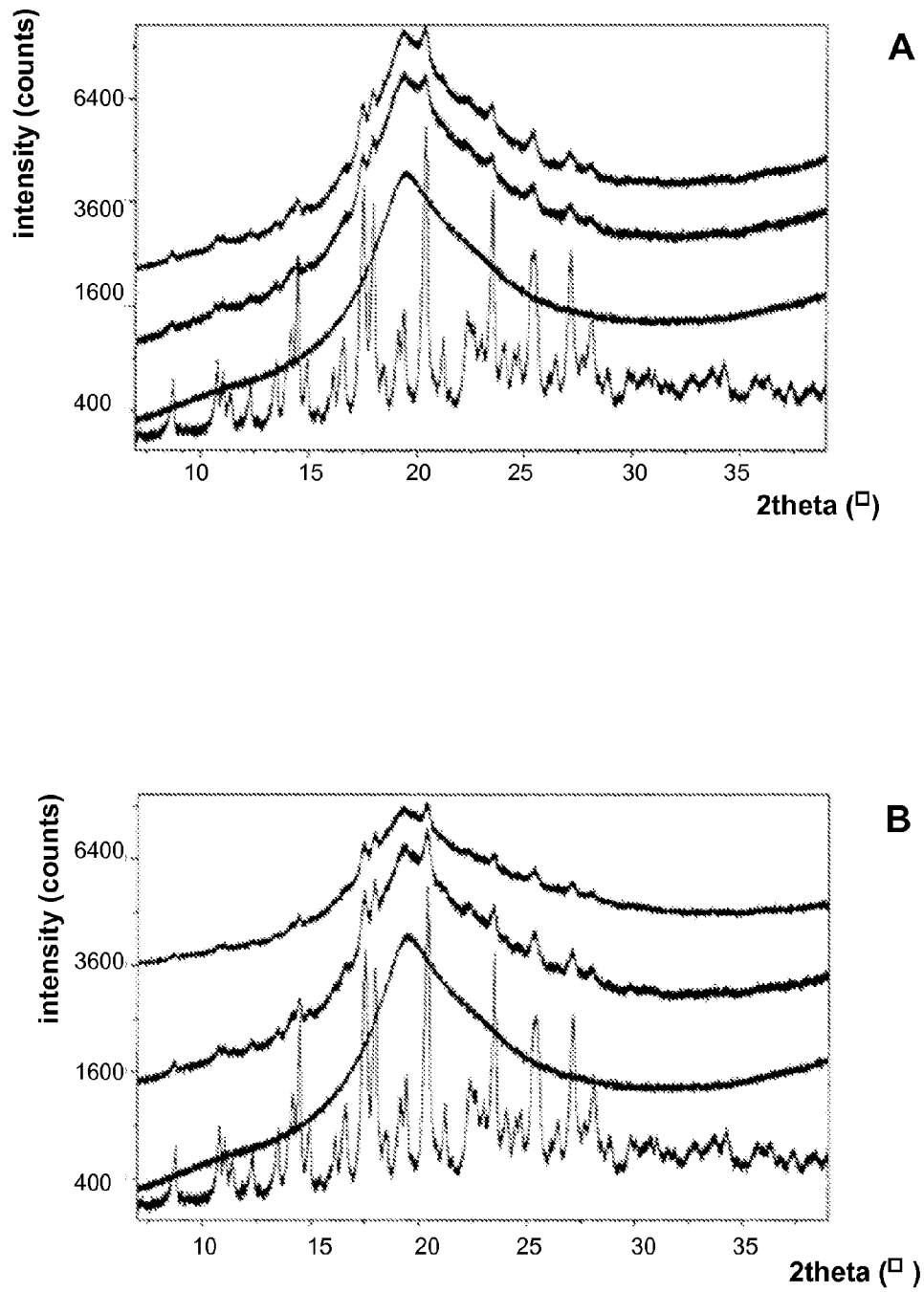
FIG. 4A: XRPDs of the following samples from top to bottom: A: 10% itraconazole in Kollicoat IR (Kollicoat IR from top, itraconazole from side), B: 10% itraconazole in Kollicoat IR (Kollicoat IR from side, itraconazole from top), C: spray dried Kollicoat IR, D: crystalline itraconazole.
FIG. 4B: XRPDs of the following samples from top to bottom: A: 60% itraconazole in Kollicoat IR (Kollicoat IR from top, itraconazole from side), B: 60% itraconazole in Kollicoat IR (Kollicoat IR from side, itraconazole from top), C: spray dried Kollicoat IR, D: crystalline itraconazole.

FIG. 4 shows the X-ray diffractograms for the solid dispersions with the lowest and the highest drug load, 10 and 60% respectively, obtained according to method 1. All solid dispersions showed itraconazole diffraction peaks, indicating the presence of a crystalline itraconazole phase. This explains, at least partially, the poor dissolution results. No differences were observed between the two modes of connecting the solutions to the spray nozzle. But, one would expect larger diffraction peaks for the samples containing 60% of itraconazole (FIG. B) than for the samples with a drug load of 10% (FIG. A). However, the intensity of the itraconazole peaks is similar for both compositions, which implies that the relative degree of crystallinity of itraconazole is higher in the samples with 10% than in the samples with 60% of itraconazole.

Figure 6:
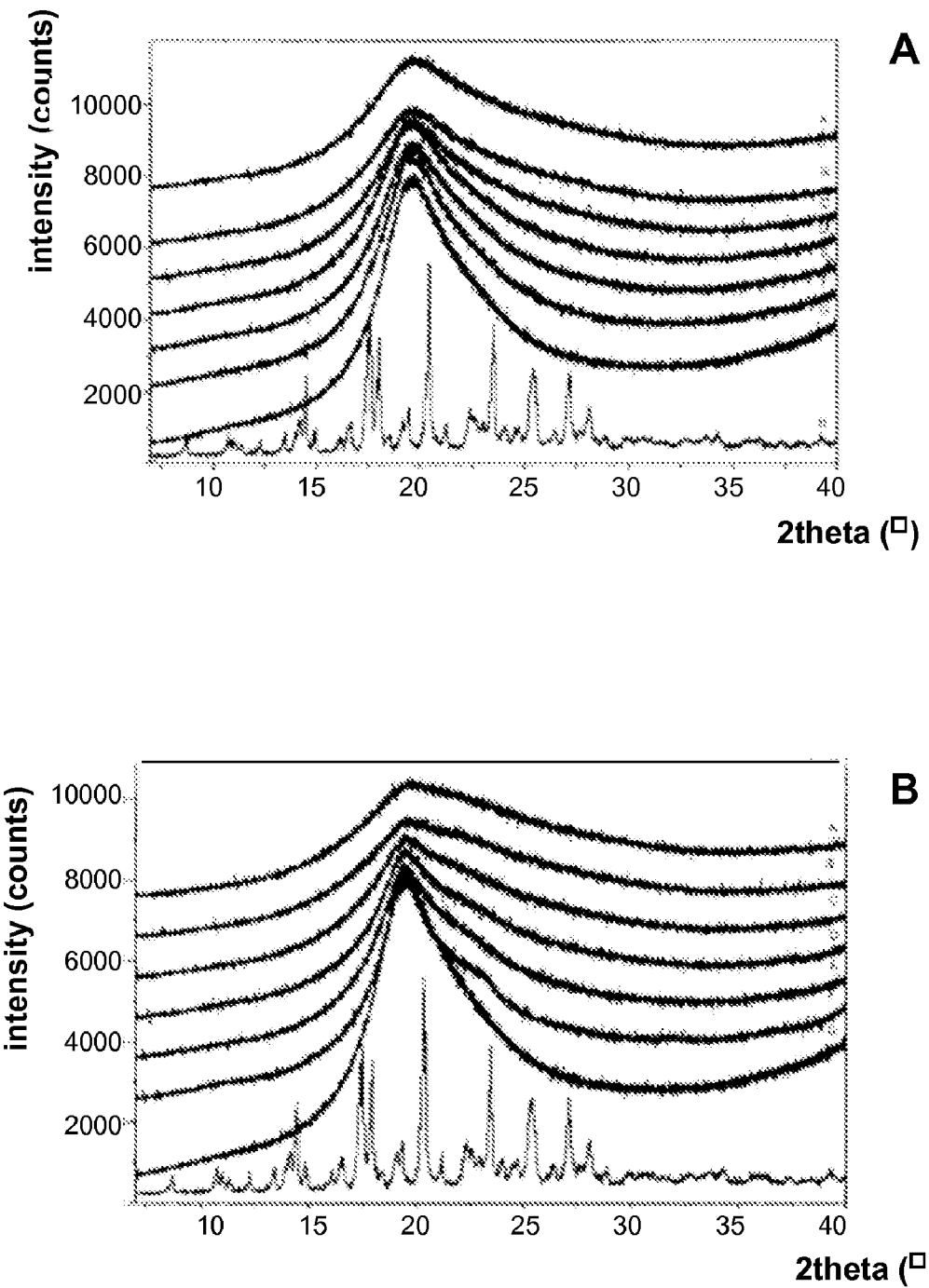
FIG. 6A: XRPD overlays itraconazole and Kollicoat IR solid dispersions spray dried from a ternary non acidic solvent with from top to bottom: A: 60% itraconazole in Kollicoat IR, B: 50% itraconazole in Kollicoat IR, C: 40% itraconazole in Kollicoat IR, D: 30% itraconazole in Kollicoat IR, E: 20% itraconazole in Kollicoat IR, F: 10% itraconazole in Kollicoat IR, G: kollicoat IR, H: crystalline itraconazole.
FIG. 6B: XRPD overlays itraconazole and Kollicoat IR solid dispersions spray dried from a ternary acidic solvent with from top to bottom: A: 60% itraconazole in Kollicoat IR, B: 50% itraconazole in Kollicoat IR, C: 40% itraconazole in Kollicoat IR, D: 30%.

FIG. 6 shows the X-ray diffractograms of the solid dispersions spray dried from acidic and non acidic ternary solvents according to method 2. All solid dispersions were X-ray amorphous and the amorphous halo becomes broader as the amount of itraconazole increases. Closer investigation of the amorphous halo leads to the observation that apart from the main broad reflection at ca. 19.3° 2θ an additional broad shoulder at ca. 23° 2θ is clearly present in the diffractogram of the 10/90 w/w itraconazole/Kollicoat IR solid dispersion spray dried from an acidic solution. This X-ray pattern corresponds well to the diffractogram of pure unprocessed Kollicoat IR, indicating that the structure of the polymer in the solid dispersion is similar to the structure of the unprocessed polymer when spray dried from an acidic solution. When spray dried from a non-acidic ternary water/dichloromethane/ethanol solution this shoulder disappears and only the main reflection at 19.3° 2θ remains, indicating that the internal structure of Kollicoat IR changes upon spray drying and becomes more amorphous.

The invention claimed is:

1. A method of preparing a solid dispersion of a polyvinyl alcohol-polyethylene glycol graft copolymer (PVA-PEG graft co-polymer), with a BCS Class II drug or a BCS Class IV drug, said method comprising
    a) dissolving the polyvinyl alcohol-polyethylene glycol graft copolymer (PVA-PEG graft co-polymer) separately in a water/first alcohol mixture; and
    b) dissolving the BCS Class II drug or the BCS Class IV drug in a mixture of a second alcohol with a non alcoholic organic solvent in which the compound has an high solubility; and
    c) mixing both solutions to obtain a third solution with a total amount of solved solid of 0.01 g to 15 g per 100 ml; and
    d) spray drying the third solution.

2. The method according to claim 1, wherein the two solutions in step c) are mixed for 1 to 30 minutes, prior to spray drying.

3. The method according to claim 1, wherein the first alcohol in step a) is selected from the group consisting of ethanol, n-butanol, isopropanol, n-propanol, and methanol, or mixtures thereof.

4. The method according to claim 1, wherein the second alcohol in step b) is selected from the group consisting of ethanol, n-butanol, isopropanol, n-propanol, methanol, 2-propanol, and hexafluoroisopropanol, or mixtures thereof.

5. The method according to claim 1, wherein the first alcohol is the same as the second alcohol.

6. The method according to claim 1, wherein the non-alcoholic solvent in step b) is selected from the group consisting of halogenated hydrocarbons, ether, aliphatic hydrocarbons, aromatic hydrocarbons, polar aprotic solvents, and organic acids, and mixtures thereof.

7. The method according to claim 6, wherein the non-alcoholic solvent in step b) is selected from the group consisting of dichloromethane, 1,4-dioxane, tetrahydrofuran, N-methyl-pyrrolidinone, chloroform, acetone, acetonitrile, dimethylformamide, dimethylsulfoxide, hexane, benzene, toluene, diethyl ether, and ethyl acetate, and mixtures thereof.

8. The method according to claim 1, wherein the ratio of water to first alcohol in step a) is in the range between 30/50 to 50/30 v/v.

9. The method according to claim 1, wherein the ratio of alcohol to non-alcoholic solvent in step b) is in the range between 30/50 to 50/30 v/v.

10. The method according to claim 1, wherein the concentration of the BCS class II drug or BCS class IV drug in the mixture of the first and second solutions is in the range between 10 and 150 mg/ml.

11. The method according to claim 1, wherein at least one inorganic acid or at least one organic acid is present in the third solution to achieve an acid pH.

12. The method according to claim 11, wherein the inorganic acid or organic acid is selected from the group consisting of hydrochloric or hydrobromic acid, sulfuric acid, nitric acid, phosphoric acid, acetic acid, propanoic acid, hydroxyacetic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, and palmoic acid.

13. The method according to claim 1, wherein at least one inorganic base or at least one organic base is added to the second solution in step b).

14. The method according to claim 13, wherein the inorganic base or organic base is selected from the group consisting of sodium hydroxide, sodium hydride, potassium hydroxide, pyridine, morpholine, N-methyl-morpholine, triethylamine, N,N-di-isopropyl-ethylamine, and dimethylamine.

15. The method according to claim 1, wherein the first alcohol in step a) is selected from the group consisting of ethanol, n-butanol, isopropanol, n-propanol and, methanol, or mixtures thereof; the second alcohol in step b) is selected from the group consisting of ethanol, n-butanol, isopropanol, n-propanol, methanol, 2-propanol, and hexafluoroisopropanol, or mixtures thereof; the non-alcoholic solvent in step b) is selected from the group consisting of dichloromethane, 1,4-dioxane, tetrahydrofuran, N-methyl-pyrrolidinone, chloroform, acetone, acetonitrile, dimethylformamide, dimethylsulfoxide, hexane, benzene, toluene, diethyl ether, and ethyl acetate, and mixtures thereof; and wherein at least one inorganic acid or at least one organic acid is present in the third solution to achieve an acid pH; and wherein at least one inorganic base or at least one organic base is added to the second solution in step b).

16. The method according to claim 15, wherein the first alcohol is the same as the second alcohol.

17. The method according to claim 15, wherein the ratio of water to first alcohol in step a) is in the range between 30/50 to 50/30 v/v and the ratio of alcohol to non-alcoholic solvent in step b) is in the range between 30/50 to 50/30 v/v; and wherein the concentration of the BCS class II drug or BCS class IV drug in the mixture of the first and second solutions is in the range between 10 and 150 mg/ml.

18. The method according to claim 15, wherein the inorganic acid or organic acid is selected from the group consisting of hydrochloric or hydrobromic acid, sulfuric acid, nitric acid, phosphoric acid, acetic acid, propanoic acid, hydroxyacetic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and palmoic acid; and wherein the inorganic base or organic base is selected from the group consisting of sodium hydroxide, sodium hydride, potassium hydroxide, pyridine, morpholine, N-methyl-morpholine, triethylamine, N,N-di-isopropyl-ethylamine, and dimethylamine.

19. The method according to claim 1, wherein the BCS class H drug is selected from the group consisting of itraconazole, fluconazole, terconazole, ketoconazole, saperconazole, sulfasalazine, griseofulvin, griseoverdin, atovaquone, cyclosporine, digoxin, spironolactone, ibuprofen, ritonavir, nevirapine, lopinavir, clofazinine, diloxanide furoate, glibenclamide, nefidepine, danazol, carbamzazepine, and acyclovir; and wherein the BCS class IV drug is selected from the group consisting of acetazolamide, furosemide, tobramycin, cefuroxmine, allopurinol, dapsone, doxycycline, paracetamol, nalidixic acid, clorothiazide, tobramycin, cyclosporin, tacrolimus, paclitaxel, a prostaglandine, a proteinase inhibitor, a cytotoxic, a metallocene, a lipid-drug conjugate, chloroquine, mefloquine, primaquine, vancomycin, vecuronium, pentamidine, metronidazole, nimorazole, tinidazole, atovaquone, and buparvaquone.

20. The method according to claim 19, wherein the prostaglandine is prostaglandine E2, prostaglandine F2, or prostaglandine E1;

wherein the proteinase inhibitor is indinavir, nelfinavir, or saquinavir; wherein the cytotoxic is doxorubicine, daunorubicine, epirubicine, idarubicine, zorubicine, mitoxantrone, amsacrine, vinblastine, vincristine, vindesine, dactiomycine, or bleomycine; wherein the metallocene is titanium metallocene dichloride; and wherein the lipid-drug conjugate is diminazene stearate or diminazene oleate.

* * * * *

UNITED STATES PATENT AND TRADEMARK OFFICE
CERTIFICATE OF CORRECTION

PATENT NO. : 8,216,495 B2  
APPLICATION NO. : 12/934232  
DATED : July 10, 2012  
INVENTOR(S) : Janssens et al.

It is certified that error appears in the above-identified patent and that said Letters Patent is hereby corrected as shown below:

Column 27, Claim 1 b), Line 38, replace "an high" with --a high--.

Signed and Sealed this  
Twenty-fifth Day of September, 2012

David J. Kappos  
*Director of the United States Patent and Trademark Office*